US006224566B1

(12) United States Patent
Loeb

(10) Patent No.: US 6,224,566 B1
(45) Date of Patent: May 1, 2001

(54) METHOD AND DEVICES FOR CREATING A TRAP FOR CONFINING THERAPEUTIC DRUGS AND/OR GENES IN THE MYOCARDIUM

(75) Inventor: Marvin P. Loeb, Huntington Beach, CA (US)

(73) Assignee: Cardiodyne, Inc., Irvine, CA (US)

( * ) Notice: Subject to any disclaimer, the term of this patent is extended or adjusted under 35 U.S.C. 154(b) by 0 days.

(21) Appl. No.: 09/305,129

(22) Filed: May 4, 1999

(51) Int. Cl.[7] .................................................. A61B 17/20
(52) U.S. Cl. .............................. 604/22; 604/20; 604/239; 606/15; 606/16
(58) Field of Search ................................... 606/7, 15, 16, 606/12; 604/20, 21, 22, 164, 264, 95, 239

(56) References Cited

U.S. PATENT DOCUMENTS

| 4,773,413 | 9/1988 | Hussein et al. ................ 128/303.1 |
| 5,242,438 | 9/1993 | Saadatmanesch et al. ........... 606/15 |
| 5,328,470 | 7/1994 | Nabel et al. ......................... 514/44 |
| 5,389,096 | 2/1995 | Aita et al. .............................. 606/15 |
| 5,532,143 | 7/1996 | Grosveld et al. .................. 435/69.1 |
| 5,554,152 | 9/1996 | Aita et al. ................................ 606/7 |
| 5,607,401 | * 3/1997 | Humphrey ........................... 604/239 |
| 5,661,133 | 8/1997 | Leiden et al. ........................... 514/44 |
| 5,685,820 | * 11/1997 | Riek et al. ........................... 600/114 |
| 5,698,531 | 12/1997 | Nabel et al. ........................... 514/44 |
| 5,707,969 | 1/1998 | Nabel et al. ........................... 514/44 |
| 5,792,453 | 8/1998 | Hammond et al. ............... 424/93.21 |
| 5,837,511 | 11/1998 | Falck-Pedersen et al. ....... 435/172.3 |
| 5,840,059 | 11/1998 | March et al. ........................... 604/53 |
| 5,846,947 | 12/1998 | Behr et al. ............................. 514/44 |
| 5,849,572 | 12/1998 | Glorioso et al. ................... 435/320.1 |
| 5,849,718 | 11/1998 | Grosveld et al. ...................... 514/44 |
| 5,849,997 | 12/1998 | Grosveld et al. ......................... 800/2 |
| 5,876,373 | * 12/1999 | Giba et al. ............................. 604/95 |
| 5,964,757 | * 10/1999 | Ponzi ...................................... 606/45 |
| 5,999,678 | * 12/1999 | Murphy-Chutorian et al. ..... 385/117 |

OTHER PUBLICATIONS

Mirhoseini M., Cayton M. M., "Revascularization of the Heart by Laser" *J Microsurg* 2:253, Jun., 1981.

(List continued on next page.)

*Primary Examiner*—Anthuan T. Nguyen
*Assistant Examiner*—Jerry Thissell
(74) *Attorney, Agent, or Firm*—Olson & Hierl, Ltd.

(57) ABSTRACT

Devices and methods for effective administration of therapeutic drugs or gene therapy to the myocardium is achieved by creating a trap or pocket within the myocardium for confining the injected therapeutic. The pocket can be created using mechanical and light energy, or other means.

22 Claims, 16 Drawing Sheets

OTHER PUBLICATIONS

Folkman and Shing, *J. Biochemistry* 267(16):10931–10934, 1992.

Thomas, "Vascular Endothelial Growth Factor, a Potent and Selective Angiogenic Agent", *J. Biochemistry* 271(2):603–606, 1996.

Abraham, J, et al, "Nucleotide Sequence of a Bovine Clone Encoding the Angiogenic Protein, Basic Fibroblast Growth Factor" *Science,* vol. 233, 545–548, 1986.

Schumacher, B et al., "Induction of Neoangiogenesis in Ischemic Myocardium by Human Growth Factors" *Circulation,* 97: 645–650 (1998).

Berlener, KL, "Development of adenovirus vectors for the expression of heterologous genes" *Biotechniques* 6:616–629, 1988.

Ziverbel, JA, et al., "High–level recombinant gene expression in rabbit endothelial cells transduced by retroviral vectors," *Science,* 243: 220–222, 1989.

Stratford–Perricaudet, LD, "Evaluation of the transfer and expression in mice of an enzyme–encoding gene using a human adenovirus vector" *Hum. Gene Ther.* 1:241–256, 1990.

Mulligan, RC, "The Basic Science of Gene Therapy", *Science,* 260:926–932 (1993).

Suri, C et al., "Increased Vascularization in Mice Overexpressing Angiopoetin–1" *Science,* vol. 282, 468–471, Oct. 1998.

Feldman et al., "Percutaneous Adenovirus–mediated Gene Delivery to Normal and Atherosclerotic Arteries In Vivo: a Comparative Study" *Circulation* 90(4), part 2:I–517, Abstract #2783, 1994.

Pastore, Christopher et al., "Intraluminal Delivery of Pluronic Gel Enhances Adenovirus–Mediated Arterial Gene Transfer: a Morphometric Study" *Circulation* 90(4), part 2:I–517, Abstract #2782, 1994.

Schulick, Andrew et al., "A Therapeutic Window for In Vivo Adenoviral–Mediated Gene Transfer" *Circulation* 90(4), part 2:I–516, Abstract #2778, 1994.

Pili, Roberto et al., "Angiogenesis Induced by Adenovirus––mediated Gene Transfer of Secreted and Non–Secreted Forms of Acidic Fibroblast Growth Factor" *Circulation* 90(4), part 2:I–516, Abstract #2777, 1994.

Blazing, MA et al., "A New Adenoviral Vector With Enhanced Expression Characteristics" *J. Invest. Med.* 43 Supplement: 278A, Abstract, 1995.

Adams & Wang et al., "Replication Defective Adenovirus Enables Transduction By Retroviral Vectors of Cells Outside Their Host Range" *J. Cellular Biochem.* Supplement 18A, Abstract DZ100, p. 222, 1994.

Armentano, D., et al., "Second Generation Adenovirus Vectors for Cystic Fibrosis Gene Therapy" *J. Cellular Biochem.* Supplement 18A, Abstract DZ102, p. 222, 1994.

Williams, RS, "Southwestern Internal Medicine Conference: Prospects for Gene Therapy of Ischemic Heart Disease", *Am. J. Med. Sciences,* 306(2): 126–136, 1993.

Marsha F. Goldsmith, in Medical News & Perspectives, "Tomorrow's Gene Therapy Suggests Plenteous, Potent Cardiac Vessels", *JAMA* vol. 268, No. 23, p. 3285–3286, 1992.

Leclerc, G, et al., "Percutaneous Arterial Gene Transfer in a Rabbit Model", *J. Clin. Invest.,* 90: 936–944 (1992).

Barr, E, et al., "Efficient catheter–mediated gene transfer into the heart using replication–defective adenovirus", *Gene Therapy* 1:51–58, 1994.

Lin, H., et al., "Expression of recombinant genes in myocardium after direct injection of DNA" *Circulation* 82:2217–2222, 1990.

Giordano, FJ et al., "Reduced Myocardial Ischemia After Recombinant Adenovirus Mediated In–Vivo Fibroblast Growth Factor–5 Gene Transfer" *J. Invest. Med.* 43 Supplement: 278A, Abstract, 1995.

Barr, E and Leiden, "Systemic delivery of recombinant proteins by genetically modified myoblasts" *Science* 254:1507–1509, 1991.

Barr, E, et al. "Induction of angiogeneses following in–vivo gene transfer into myocardium" *Circulation* vol. 84, No. 4, Supplement II, p. II–420, Abst. #1673, 1991.

Stratford–Perricaudet, LD, et al. "Widespread long–term gene transfer the mouse skeletal muscles and heart" *J. Clin. Invest.* 90:626–630, 1992.

French, Brent et al., "Feasibility and Limitations of Direct In Vivo Gene Transfer into Porcine Myocardium Using Replication–Deficient Adenoviral Vectors" *Circulation* 90(4), part 2:I–517, Abstract #2785, 1994.

Losordo, DW, et al., "Gene Therapy for Myocardial Angiogenesis", *Circulation,* 98: 2800–2804 (1998).

Fleischer, KJ et al., "One–month histologic response of transmyocardial laser channels with molecular intervention" *Ann Thorac. Surg.* 62(4): 101–8, 1996.

Sayeed–Shah, V, et al. ("Complete Reversal of Ischemic Wall Motion Abnormalities by Combined Use of Gene Therapy With Transmyocardial Laser Revascularization" *J. Thorac. Cardiovasc. Surg.* 116(5): 763–9, 1998.

Lee G. et al., "Effects of Laser Irradiation Delivered by Flexible Fiberoptic System on the Left Ventricular internal Myocardium," *Am Heart J.,* Sep., 1983.

Gimenez–Gallego et al., "Brain–derived acidic fibroblast growth factor: complete amino acid sequence and homologies" *Science* 230: 1385–1388, 1985.

Thompson et al., Site–directed neovessel formation in vivo *Science* 241: 1349–1352 (1988).

Folkman et al., "Angiogenic Factors" *Science* 235: 442–447 (1987).

Hariawala and Sellke "Angiogenesis and the heart: therapeutic implications" *J. R. Soc. Med.* 90: 307–311 (1997).

Yanagisawa–Miwa et al., "Salvage of infarcted myocardium by angiogenic action of basic fibroblast growth factor" *Science* 257: 1401–1403 (1992).

Harada et al., "Basic fibroblast growth factor improves myocardial function in chronically ischemic porcine hearts" *J. Clin. Invest.* 94: 623–630 (1994).

Banai et al., "Angiogenic–induced enhancement of collateral blood flow to ischemic myocardium by vascular endothelial growth factor in dogs" *Circulation* 89,5: 2183–2189 (1994).

Gao, M. et al., "Increased expression of adenylylcyclase type VI proportionately increases beta–adrenergic receptor––stimulated production of cAMP in neonatal rat cardiac myocytes", *PNAS(USA),* 95(3):1038–43.

Sayeed–Shah, V, et al. "Complete Reversal of Ischemic Wall Motion Abnormalities by Combined Use of Gene Therapy With Transmyocardial Laser Revascularization" Program of the Annual Meeting May 3–6, 1998, p. 70–71.

Hariwala et al. "VEGF improves Myocardial blood flow but produces EDRF–mediated hypotension n porcine hearts" *J. Surgical Res.,* 63:77–82 (1996).

\* cited by examiner

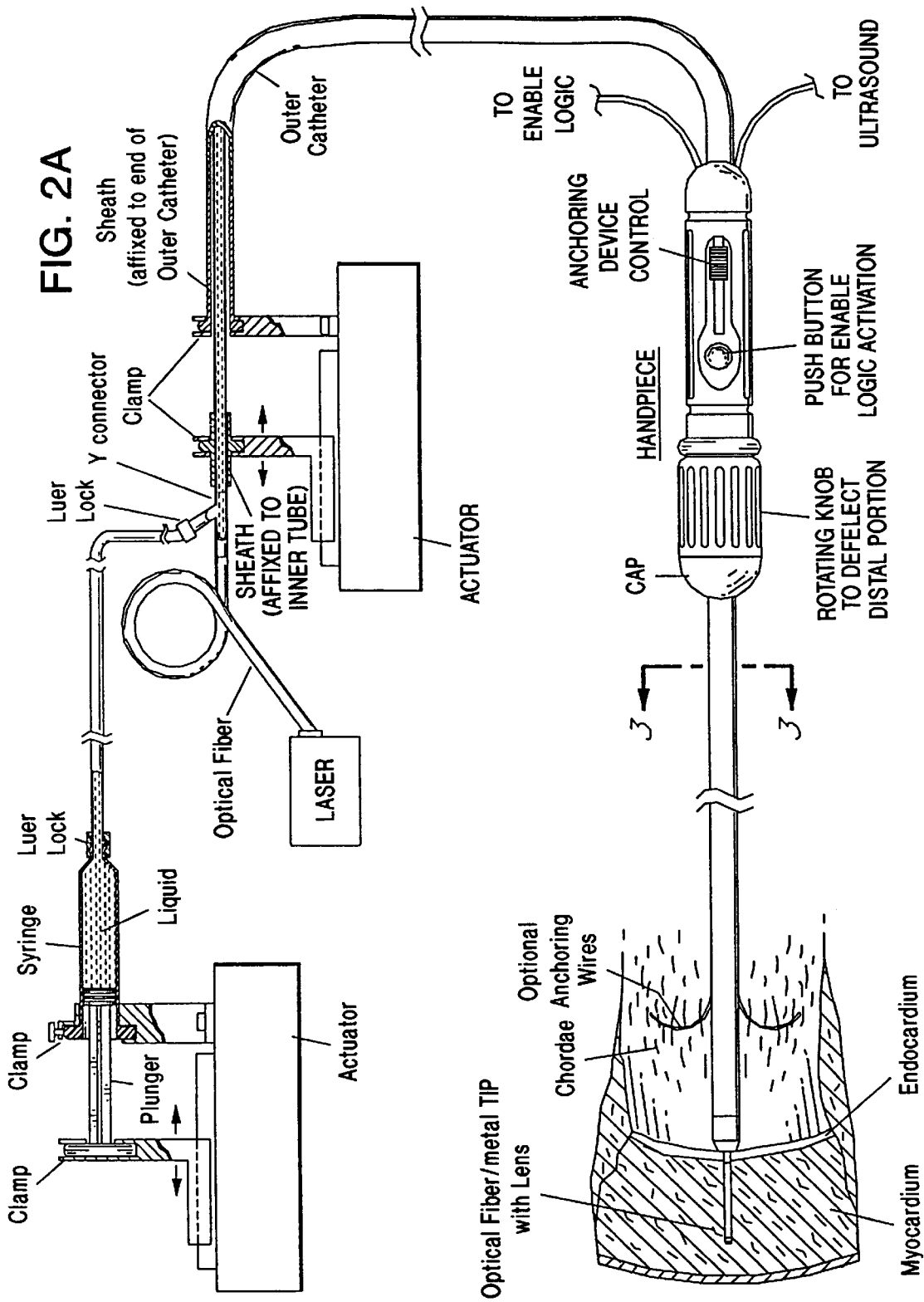

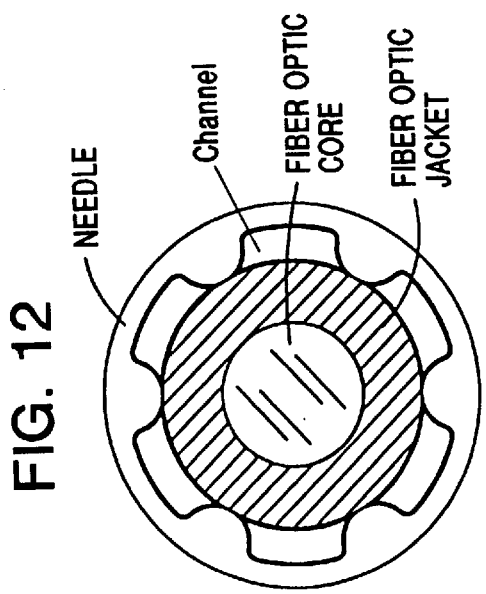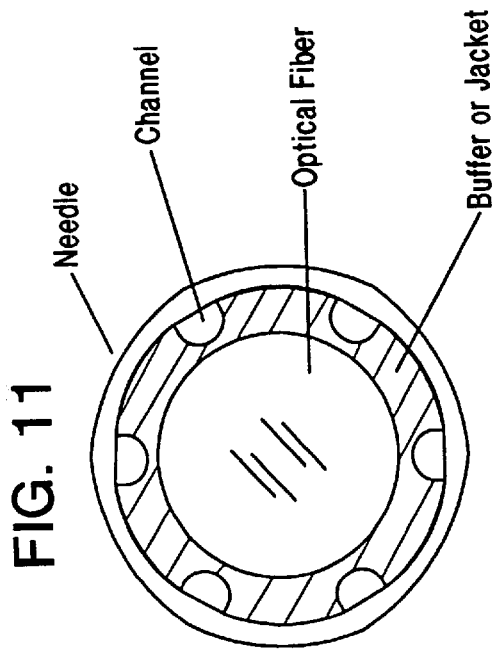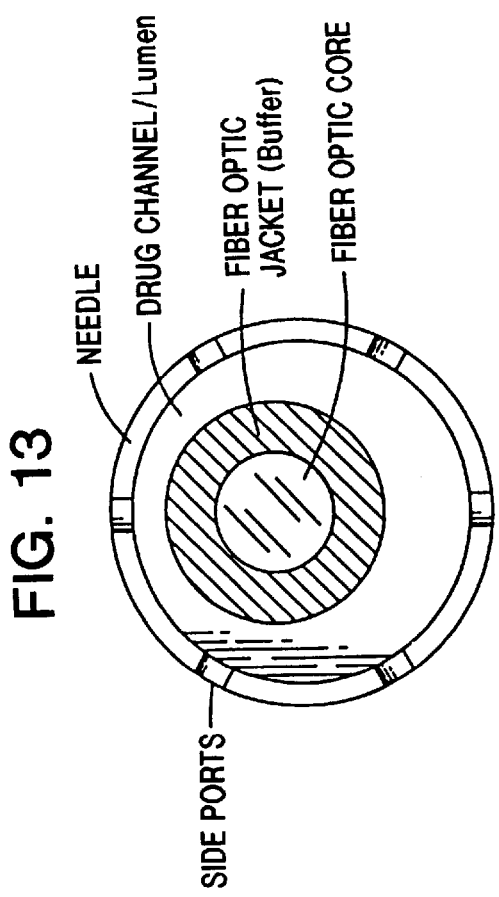
FIG. 11
FIG. 12
FIG. 13

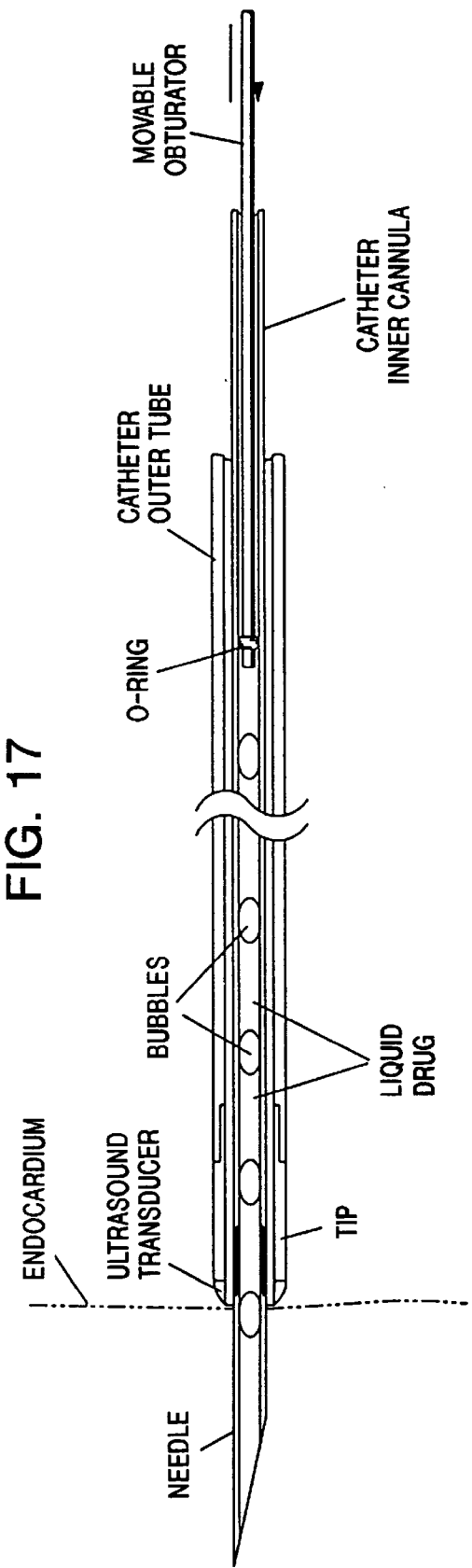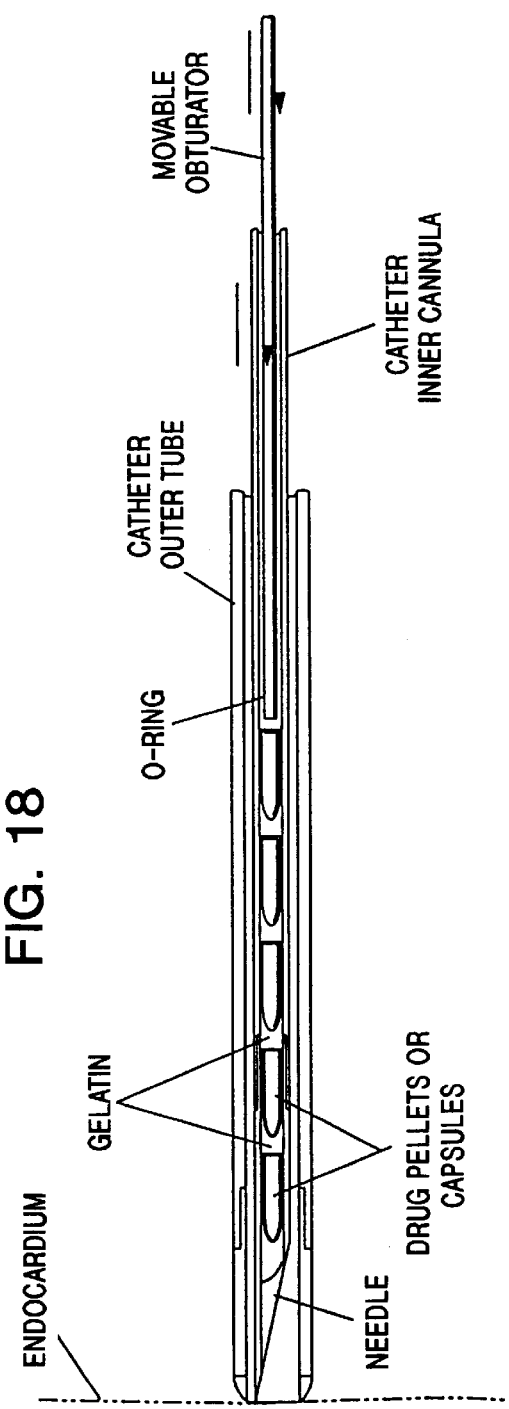

METHOD AND DEVICES FOR CREATING A TRAP FOR CONFINING THERAPEUTIC DRUGS AND/OR GENES IN THE MYOCARDIUM

TECHNICAL FIELD OF THE INVENTION

The present invention relates to devices and methods for therapeutic treatment of the heart. In particular, the present invention relates to devices for creating a pocket in the myocardium of a mammalian heart and depositing therein therapeutic substances such as angiogenic growth factors or genes coding for such growth factors, or other desirable therapeutics or gene therapy vectors.

BACKGROUND OF THE INVENTION

Coronary Heart Disease and TMLR—Coronary Heart disease is prevalent in modern society, wherein the reduced blood supply to the heart, due to blockages in one or more of the coronary arteries, is the most common cause of heart attacks and death from heart disease. Currently, surgical intervention using coronary artery bypass graft surgery and/or coronary balloon angioplasty is the most common procedure to treat this condition.

Recently, procedures for modifying a human heart to imitate the blood delivery method of a lizard heart is currently being used as an alternative or adjunct to both coronary artery bypass graft surgery and coronary balloon angioplasty. Normally, a person can only undergo coronary bypass surgery twice, since the risks will begin to outweigh the benefits after that point. Thus, in the past, a patient who has already had two coronary bypass surgeries was left with no recourse. Others patients have failed repeated coronary balloon angioplasties, and many persons are not suitable candidates for coronary bypass surgery or coronary balloon angioplasty. These persons likewise are left with no treatment options.

Early attempts to create direct blood supply to the myocardium of mammals, known as transmyocardial revascularization (TMR), consisted of producing tiny channels in mammalian and human hearts with needles or pre-heated wires. These methods met with limited success since, although the channels closed by clotting at the outside surface of the heart due to exposure to air, and did allow for some internal blood delivery, the channels soon healed over entirely and failed to continue to enhance the blood supply. Early attempts were also made to graft a blood vessel from the aorta directly into the heart muscle to provide an internal source of blood. While some benefits were seen, the surgery was technically demanding and the procedure was eclipsed by the introduction of coronary artery bypass graft surgery.

To overcome these problems, Mahmood Mirhoseini and Mary M. Cayton attempted transmyocardial revascularization using a pulsed $CO_2$ laser to make the channels. This procedure has come to be known as transmyocardial laser revascularization (TMLR). Mirhoseini M., Cayton M. M., "Revascularization of the Heart by Laser" *J Microsurg* 2:253, June, 1981. The laser forms each channel by vaporizing a passageway completely through the wall of the heart. The relatively clean channel formed by the laser energy prevents the channel from healing over, and the channel either closes by clotting at the heart's outer surface, due to exposure to air, or manual pressure can be applied until bleeding from the channel ceases. In some cases, a suture is required to close the channel. However, if bleeding cannot be stopped, or if bleeding resumes at a later time, after the patient is no longer in surgery, the patient may require emergency surgery or may die.

While most, if not all of the laser created channels close over time, the reduction in angina pain achieved by TMLR increases over a period of six months and is stable for at least an additional six months. In animal studies, it was found that extensive angiogenesis was seen in the area surrounding the channels, which is belied to be the main reason for TMLR's increasing benefit over six months and further extended benefit.

Since the body stores only small amounts of angiogenic growth factors in the heart, it is obvious that supplementing the body's supply of natural (endogenous) growth factors with growth factors produced by recombinant technology or to infect the myocardium with genes able to cause myocardial cells to express the growth factors, could yield greater angiogenesis and thus greater therapeutic benefits.

Angiogenesis and Atherosclerosis—Angiogenesis is the fundamental process by which mammalian systems form new blood vessels in normal growth and in response to injury. Normal angiogenesis is tightly regulated, and uncontrolled angiogenesis has been implicated in many disease states, including cancer. Specific angiogenic growth factors and other substances have been identified in the art, such as vascular endothelial growth factor or VEGF, fibroblast growth factor or FGF, and angiopoetin. (See for example Folkman and Shing, 1992, *J. Biochemistry* 267(16):10931–10934; Thomas, 1996, *J. Biochemistry* 271(2):603–606).

Initial work in the area of angiogenesis revolved around the discovery and characterization of angiogenic agents. For example, Abraham, J, et al ("Nucleotide Sequence of a Bovine Clone Encoding the Angiogenic Protein, Basic Fibroblast Growth Factor" *Science*, Vol. 233, 545–548, 1986) taught the nucleotide sequence of acidic FGF (aFGF), and the structures of acidic FGF (aFGF or FGF-I) and basic FGF (bFGF).

Recently it has been shown that the administration of purified human FGF-I was able to induce neoangiogenesis in ischemic myocardium, after injection concurrent with internal mammary artery (IMA)/left anterior descending coronary artery (LAD) anastomosis surgery. Schumacher, B et al., "Induction of Neoangiogenesis in Ischemic Myocardium by Human Growth Factors" *Circulation*, 97: 645–650 (1998).

Gene Therapy—With the identification and characterization of various angiogenic agents, it was possible to purse direct molecular intervention in vivo of the processes of neovascularization. Gene therapy has been a long desired goal of biomedical science, but effective introduction of genes causing the expression of VEGF or FGF into cells of the myocardium takes lengthy exposure which is not practical in a beating heart. Inserting an angiogenic gene into the genome of a replication deficient virus, which retains its ability to infect cells, was proposed to overcome this problem. Berlener, K L ("Development of adenovirus vectors for the expression of heterologous genes" *Biotechniques* 6:616–629, 1988) was one of the earliest reports on the use of such viruses for gene transfer.

Work in the art of gene expression vectors and delivery has advanced greatly in the last few years. For example, Ziverbel, J A, et al., ("High-level recombinant gene expression in rabbit endothelial cells transduced by retroviral vectors," *Science*, 243: 220–222, 1989) demonstrated the practical use of retroviral vectors to carry genes into endothelial cells. However, prior and subsequent work has shown that the use of retrovirus vectors is problematic, as complete and permanent deactivation of the retrovirus cannot be assured. Stratford-Perricaudet, L D, ("Evaluation of the transfer and expression in mice of an enzyme-encoding gene using a human adenovirus vector" *Hum. Gene Ther.* 1:241–256, 1990) was also an early report of human adenovirus gene therapy work. Methods for delivery of gene therapy to specific targets has met with substantial progress, however specific technical issues still require further work (see Mulligan, R C, "The Basic Science of Gene Therapy", *Science*, 260: 926–932 (1993), for review).

Continued research on gene therapy and angiogenic factors have yielded information about coordinated action of various factors, for example, Suri, C et al. ("Increased Vascularization in Mice Overexpressing Angiopoetin-1" *Science*, Vol. 282, 468–471, October 1998), showed that angiopoetin-1 is necessary to mature and maintain new vessels initially created by introduction of VEGF or aFGF. This work demonstrates that additional substances, such as angiopoietin-1, can be used to maintain the integrity of the newly created vessels for a long term effect.

Continued research involving treating blood vessels to either enhance or inhibit angiogenesis related to atherosclerosis using gene therapy has yielded useful results. For example, Feldman et al., "Percutaneous Adenovirus-mediated Gene Delivery to Normal and Atherosclerotic Arteries In Vivo: a Comparative Study" *Circulation* 90(4), part 2:I-517, Abstract #2783, 1994), and Pastore, Christopher et al., "Intraluminal Delivery of Pluronic Gel Enhances Adenovirus-Mediated Arterial Gene Transfer: a Morphometric Study" *Circulation* 90(4), part 2:I-517, Abstract #2782, 1994), illustrates use of viral vectors to treat blood vessels by direct administration after denuding the blood vessel wall. Schulick, Andrew et al., "A Therapeutic Window for In Vivo Adenoviral-Mediated Gene Transfer" *Circulation* 90(4), part 2:I-516, Abstract #2778, 1994), illustrate various viral concentrations beyond which efficiency is not increased, using a rat carotid artery system. Other in vitro experiments also demonstrate systems for evaluating viral expression vectors, for example Pili, Roberto et al., ("Angiogenesis Induced by Adenovirus-mediated Gene Transfer of Secreted and Non-Secreted Forms of Acidic Fibroblast Growth Factor" *Circulation* 90(4), part 2:I-516, Abstract #2777, 1994), demonstrated the use of aFGF encoding viral vectors to induce angiogenesis from cultured human umbilical vein endothelial cells. Blazing, M A et al., ("A New Adenoviral Vector With Enhanced Expression Characteristics" *J. Invest. Med.* 43 Supplement: 278A, 1995), examined viral transfection using a cultured vascular smooth muscle cell system. Wang, Mary et al., ("Replication Defective Adenovirus Enables Transduction By Retroviral Vectors of Cells Outside Their Host Range" *J. Cellular Biochem.* Supplement 18A, Abstract DZ100, page 222, 1994), found a 2 to 4 fold increase in infectiveness over unmodified vector. Armentano, D., et al., ("Second Generation Adenovirus Vectors for Cystic Fibrosis Gene Therapy" *J. Cellular Biochem.* Supplement 18A, Abstract DZ102, page 222, 1994) describe another improved viral vector.

Ischemic heart disease has also been identified as an attractive potential target for gene therapy intervention. As discussed by Williams, R S, ("Southwestern Internal Medicine Conference: Prospects for Gene Therapy of Ischemic Heart Disease", *Am. J. Med. Sciences*, 306(2): 126–136 (1993)), a number of pathophysiologic features or manifestations of ischemic heart disease present attractive targets for direct gene therapy, including atherosclerosis, cell proliferation, angina, and thrombosis.

Coronary Heart Disease, Angiogenesis and Infision—With greater understanding about angiogenic factors and genes expressing the same, collectively "angiogenic agents", and their potential to induce neovascularization, infusion of such angiogenic agents into one or more coronary arteries has been described to attempt increased blood supply to the heart. However, an undesirable side-effect of this route of administration is that virus is released into the general circulation.

The use of angiogenic agents and their potential for treating heart disease were discussed by Marsha F. Goldsmith ("Tomorrow's Gene Therapy Suggests Plenteous, Potent Cardiac Vessels", *JAMA* Vol. 268, No. 23, Pg. 3285–3286, 1992) in *Medical News & Perspectives* column. In this article, she discusses work by Jeffrey Leiden & Elian Barr (U. of Chicago), including naked DNA injection into cardiac and skeletal muscle and the use of an adenovirus (replication sequences deleted) vector containing an angiogenic gene which was injected into a coronary artery, infecting the entire artery.

Leclerc, G, et al., "Percutaneous Arterial Gene Transfer in a Rabbit Model", *J. Clin. Invest.,* 90: 936–944 (1992), describe approximately 50% transfection efficiency for delivering foreign DNA to balloon-injured arteries using a DNA-liposome transfection vector.

Further work by Barr, E, et al. ("Efficient catheter-mediated gene transfer into the heart using replication-defective adenovirus", *Gene Therapy* 1:51–58, 1994), showed that five days after infusion administration the virus was detected in the brain, lungs, liver, kidneys and testes. This was after a single infusion into a coronary artery at $2 \times 10^9$–$1 \times 10^{10}$ p.f.u. of adenovirus-linked gene. Thus, infusion of adenovirus-linked genes into a coronary artery resulted in the undesirable result of disseminating the angiogenic capable genes systemically, which could enable an occult tumor to grow by extending its blood vessel system.

Angiogenesis, the Heart, and Direct Injection—Attempts to directly inject angiogenic agents directly into the muscle of the heart, while attractive, have had various technical difficulties that reduces overall efficacy of gene therapy. When the therapeutic agents, in a liquid medium, are injected into the wall of a beating heart, on the next compression of the heart, much of the liquid is expelled by contraction of the muscle.

Lin, H., et al. ("Expression of recombinant genes in myocardium after direct injection of DNA" *Circulation* 82: 2217–2222, 1990), showed the feasibility of gene transfer into the cells of the myocardium by direct injection of naked DNA. However, later papers showed much higher cell penetration rates and transformation efficacy with genes incorporated into the genome of replication defective adenovirus or other viral vectors.

Giordano, F J et al., ("Reduced Myocardial Ischemia After Recombinant Adenovirus Mediated In-Vivo Fibroblast Growth Factor-5 Gene Transfer" *J. Invest. Med.* 43 Supplement: 278A, 1995), demonstrated successful infection of myocardial cells from an intracoronary injection of replication deficient viral vector encoding FGF-5.

Studies of the specific transformation of heart muscle cells was greatly advanced by the work of Barr, E and Leiden, ("Systemic delivery of recombinant proteins by genetically modified myoblasts" *Science* 254:1507–1509, 1991) who demonstrated that skeletal muscle cells of a host could be genetically modified and injected into the myocardium. This was useful since myocytes cannot be cultured in-vitro. However, it was found that injection of these cells into cardiac muscle, resulted in an inflammatory response and fibrous formations.

Barr, E, et al. ("Induction of angiogeneses following in-vivo gene transfer into myocardium" *Circulation* Vol. 84, No. 4, Supplement II, Pg. II-430, 1991) described the use of pRSV-FGF5 plasmid containing the FGF-5 gene injected into left ventricular wall of rats. The results showed that resulting capillary density was 32% higher than in control animals who were injected with the viral plasmid alone.

Stratford-Perricaudet, L D, et al. ("Widespread long-term gene transfer the mouse skeletal muscles and heart" *J. Clin. Invest.* 1992; 90:626–630) which examined lasting effects of gene transfer into such tissues.

French, Brent et al., "Feasibility and Limitations of Direct In Vivo Gene Transfer into Porcine Myocardium Using Replication-Deficient Adenoviral Vectors" *Circulation* 90(4), part 2:I-517, Abstract #2785, 1994), observed a much higher efficiency of transformation (140,000 times higher) using a viral vector versus "naked" DNA plasmid. The infiltration of transformation using the viral vector injection rarely showed up more than 5 mm from the injection site.

Similarly, angiogenic genes/viral vectors were shown to be more efficient in infecting myocardial cells than genes in a liposome delivery system.

Losordo, D W, et al., "Gene Therapy for Myocardial Angiogenesis", *Circulation*, 98: 2800–2804 (1998), describes initial clinical results with direct myocardial injection of $phVEGF_{165}$ as sole therapy for myocardial ischemia in men who had failed conventional therapy, and suffered from angina. Naked plasmid DNA encoding for VEGF was injected directly into the ischemic myocardium (anterolateral left ventricular free wall) via a mini left anterior thoracotomy (125 $\mu$g in 4 aliquots of 2.0 mL each). After about 60 days post-operation, the patients appeared to benefit from the treatment.

Several U.S. patents are related to gene therapy, viral vectors, and in particular angiogenic agents, including U.S. Pat. No. 5,849,997 (Grosveld et al.); U.S. Pat. No. 5,849,718 (Grosveld); U.S. Pat. No. 5,849,572 (Glorioso et al.); U.S. Pat. No. 5,846,947 (Behr et al.); U.S. Pat. No. 5,661,133 (Leiden et al.); U.S. Pat. No. 5,837,511 (Crystal et al.); U.S. Pat. No. 5,792,453 (Hammond et al.); U.S. Pat. No. 5,328,470 (Nabel et al.); U.S. Pat. No. 5,698,531 (Nabel et al.); U.S. Pat. No. 5,707,969 (Nabel et al.); U.S. Pat. No. 5,840,059 (March et al.,); U.S. Pat. No. 5,389,096 (Aita et al.,); and U.S. Pat. No. 5,554,152 (Aita et al.).

While a growth factor, a gene coding for a growth factor, or such a gene incorporated in a vector may be injected into an arrested heart with a simple syringe, much of the angiogenic agent would be expelled on the next contraction of a beating heart. As a result, creating a space within the heart muscle, in which the angiogenic therapeutic could repose for sufficient time for its absorption would be desirable.

TMLR and Angiogenic Agent Therapy—TMLR procedures using an adenovirus vector encoding human Profilin was not found to be effective in stimulating additional angiogenesis in a study reported by Fleischer, K J et al., ("One-month histologic response of transmyocardial laser channels with molecular intervention" *Ann Thorac. Surg.* 62(4): 101–8, 1996). The procedure appeared to create more inflammation in the tissues by stimulating release of VEGF but no additional angiogenesis.

Recently, Sayeed-Shah, V, et al. ("Complete Reversal of Ischemic Wall Motion Abnormalities by Combined Use of Gene Therapy With Transmyocardial Laser Revascularization" *J. Thorac. Cardiovasc. Surg.* 116(5): 763–9, 1998; and 1998 abstract), describe the injection of VEGF genes along with TMLR. The results indicate that they were able to normalize heart wall motion in animals in which a coronary artery was artificially constricted, a result superior to injection of the same gene or TMLR alone.

The prior art also uses several mirrors mounted on an articulating arm to reflect carbon dioxide laser energy toward the tissue to be vaporized. Maintaining the proper alignment of these mirrors at all times, however, is difficult and positioning the arm is inconvenient for the operator. Laser energy transmitted through optical fibers could eliminate this problem and avoid making a large opening into the patient's chest in order to perform the TMLR procedure.

Further, the use of lasers whose energy can be transmitted through optical fibers, such as argon-ion, have also been proposed for performing TMLR through a percutaneously inserted catheter from the inside of the heart chamber, Lee G. et al., "Effects of Laser Irradiation Delivered by Flexible Fiberoptic System on the Left Ventricular internal Myocardium," *Am Heart J.*, September, 1983.

However, if argon-ion laser energy is applied to make the channel completely through the heart wall, since such lasers are of significantly less power than the $CO_2$ laser used in TMLR, the optical fiber must be present in the heart wall for a longer period of time than diastole, when the heart's electrical activity is minimal and the heart is momentarily at rest. If the procedure cannot be completed during diastole, within approximately 0.6 seconds (at a heart rate of 60 beats per minute), between heartbeats when the heart's electrical activity is minimal, a life threatening arrhythmia may result, and mechanical damage to the heart muscle during its compression may occur.

Using a typical TMLR procedure and device, if the gene therapy agent in a liquid medium is injected into the channel in the wall of a beating heart, the next contraction of the heart muscle will force much of the agent out of the channel. Generally, it is desired that the channels be made primarily within the heart's myocardium and the inner portion of the endocardium since the myocardium and endocardium have a greater need of an alternative supply of blood than the heart's outer surface (epicardium).

The methods and apparatus of the present invention avoid the problems of the art methods of administration of angiogenic agent by creating a space or pocket within the heart muscle using a laser, which does not extend completely through the endocardium into the heart chamber, with minimal interruption of the epicardium, if the space is created from the epicardial surface of the heart, or into the epicardium or outer surface of the heart, with minimal interruption of the endocardium, if the pocket is created from the endocardial surface of the heart chamber, into which an angiogenic agent may be injected and trapped, avoiding its dissemination into the circulation.

Since the pulsed laser energy of a wavelength highly absorbed by water ($CO_2$ or Holmium:YAG, for example) or protein (Excimer, for example) causes an acoustic shock and pressure wave in the tissue, causing endogenous (naturally occurring) growth factors to be released that likewise cause neovasculorigation, a complementary angiogenic effect can be achieved.

If using an optical fiber, whose distal end is encased in a short length of double-beveled syringe needle of 18 gauge or smaller, the entry of the needle (without laser energy emission) into the heart wall creates a cut, rather than a puncture, which almost immediately seals and remains closed.

BRIEF SUMMARY OF THE INVENTION

The present invention provides a device and procedure for utilizing mechanical energy to create a passageway through the epicardium or endocardium, as the case may be, which seals more quickly and dependably than a laser created channel, and delivering sufficient laser energy only into the myocardium, to form a receptacle, i.e., a cavity, chamber, pocket, or the like, in the heart muscle which can hold therapeutic agents.

The contemplated therapeutic agents suitable for use with the invention include, but are not limited to, drugs, purified or recombinant human proteins, naked DNA genes, gene expression/therapy vectors, anti-sense nucleic acids or other such therapeutics known in the art, whether administered alone or in combinations with other agents in solution, or packaged within suitable carriers such as liposomes, microcapsules, transformed cells, viral vectors, and the like. Such suitable therapeutic agents, whether chemical or molecular biological in nature, can be useful for treating a patient's heart to induce angiogenesis, which are or can produce clot inhibiting or dissolving enzymes, that are or can produce useful enzymes, to reduce inflammation, to treat infection, or to reduce pain, among other uses.

A device suitable for the administration of a predetermined amount of the aforementioned therapeutic agent includes a catheter, which terminates at its distal end in a hollow, open-ended puncturing tip, and encases an optical fiber, operably associated with a laser energy source when in use. The puncturing tip is in fluid flow communication with the catheter and defines a fluid channel for dispensing the therapeutic agent, The optical fiber is situated within the catheter so that the distal end of the optical fiber extends into the puncturing tip. The optical fiber together with the catheter define a confined flow passageway which is in communication with the fluid channel in the puncturing tip. In this manner, a therapeutic agent is introduced into the myocardium as the therapeutic agent exits the fluid channel defined by the tip.

The device embodying the present invention is especially suitable for use in medical applications for delivering laser energy to a selected tissue site at a controlled rate in a uniform manner, so the depth of the coagulation zone surrounding the pocket and size of the pocket formed can be controlled as desired. Furthermore, the present device allows formation of uniformly or otherwise desirably shaped pockets between heartbeats in a periodically moving structure such as a human heart, from either the outside of the heart (epicardium) or from the inside of the heart chamber (endocardium).

A preferred surgical device embodying the present invention includes a source of laser energy, an optical fiber optically coupled to the source of laser energy, a hollow needle surrounding at least a portion of the distal end of the optical fiber, and a catheter surrounding at least a portion of the optical fiber communicating with the space between the needle and the optical fiber. These components can also be movably disposed within an outer catheter terminating in a handpiece, for easy handling, from which a metal cannula may extend distally. An actuator rod may be optionally provided to actuate the transmission of laser energy, when it is depressed a selected distance by contact with the heart's surface. The actuator rod can also actuate a mechanism to extend the needle, and the optical fiber contained therewithin, from the cannula into the tissue at the site where the pocket is to be formed. The pocket is formed by energizing, after the needle containing the optical fiber has penetrated a first desired distance into the tissue, a suitable laser source and passing a laser beam from the source through the optical fiber emitting laser energy as the fiber/needle moves a second, additional desired distance into the tissue and, after ceasing the emission of laser energy, injecting a therapeutic agent into the pocket created by the laser energy through the space between the needle and the optical fiber as the fiber/needle combination is being withdrawn from the pocket, after which the fiber needle withdraws the first desired distance from the tissue. The fiber/needle may be beveled and/or pointed, as in traditional syringe needles, or may be blunt but of sufficiently narrow diameter to act as a fine puncture device, where such a blunted device may also incorporate a trocar shape or beveled circumference. The tip assembly of the invention will be called, in various embodiments a fiber/tip, needle/tip, fiber/needle, or other such combination of terms, which emphasize the scope of elements which can be combined to create the tip apparatus embodied by the invention.

The pocket in the myocardium may also be similarly formed by mechanical energy, such as a rotating burr, or by delivering radio-frequency electrical energy, high intensity ultrasound energy or microwave energy at a controlled rate in a uniform manner directly onto a selected tissue site within the heart wall for creating a pocket into which a therapeutic agent can be injected and confined.

A mechanical rotating burr device embodying the present invention includes a cannula, a flexible drive cable with a distal burr such that the rotation of the drive cable translates into the rotation of the burr.

A radio-frequency electro-surgical device embodying the present invention includes a cannula, and an electrically conductive lead with a distal end/electrode within an insulated sleeve, which is received within a bore that passes through the cannula. An actuator may optionally be operably coupled to a source of energy and/or a mechanism for advancing the sleeve and lead assembly into the tissue. The lead is energized by a suitable energy source to form a desirably sized pocket within the tissue, into which the therapeutic agent is injected through the space between the lead and the sleeve as the sleeve and lead are withdrawn from the pocket. Optionally, the lead may be located within a separate channel within the cannula.

Numerous other advantages and features of the present invention will become readily apparent from the following detailed description of the invention, from the claims, and from the accompanying drawings.

BRIEF DESCRIPTION OF THE DRAWINGS

The many embodiments of devices suitable for the practice of the methods of the present invention may be better understood in view of the accompanying drawings that form part of the specification, and in which like numerals are employed to designate like parts throughout the same, in which:

FIG. 2A is a schematic diagram showing further details of the apparatus and supporting features shown in FIG. 1, showing in partial cutaway the fluid communication through the lumen of the inner catheter.

FIG. 11 is a cross sectional view showing an alternative embodiment of a needle/fiber optic device of the invention for practicing the methods of the invention wherein several fluid channels are in fluid communication with the lumen of the inner catheter, this embodiment having the optical fiber fixed within the bore of the needle, and surrounded by either buffer or a jacket.

FIG. 12 is a similar cross sectional view as shown in FIG. 13, depicting an optical fiber covered by a jacket, and the fluid communication channels being interspersed between flanges on the inner surface of the bore of the needle to fix the optical fiber in place.

FIG. 13 is similar to that depicted in FIG. 11, showing an alternative embodiment of the needle/metal tip-optical fiber of the invention, showing a fluid communication channel within the bore of the needle and side ports to allow exit of liquid, the distal end of the optical fiber being surrounded by a jacket that allows the optical fiber to be fixed within the bore of the metal tip/needle.

FIG. 17 depicts a view very similar to that of FIG. 16, showing that the aliquots of drug to be administered are separated by gaseous bubbles of a predetermined size.

FIG. 18 depicts a view similar to that of FIG. 17, showing that the drug is administered in lyophilized aliquots which can be optionally formed into bullet shaped (or otherwise elongated) pellets, or as a liquid contained within an elongated capsule.

DETAILED DESCRIPTION OF THE INVENTION

Growth Factors

Figure 1:
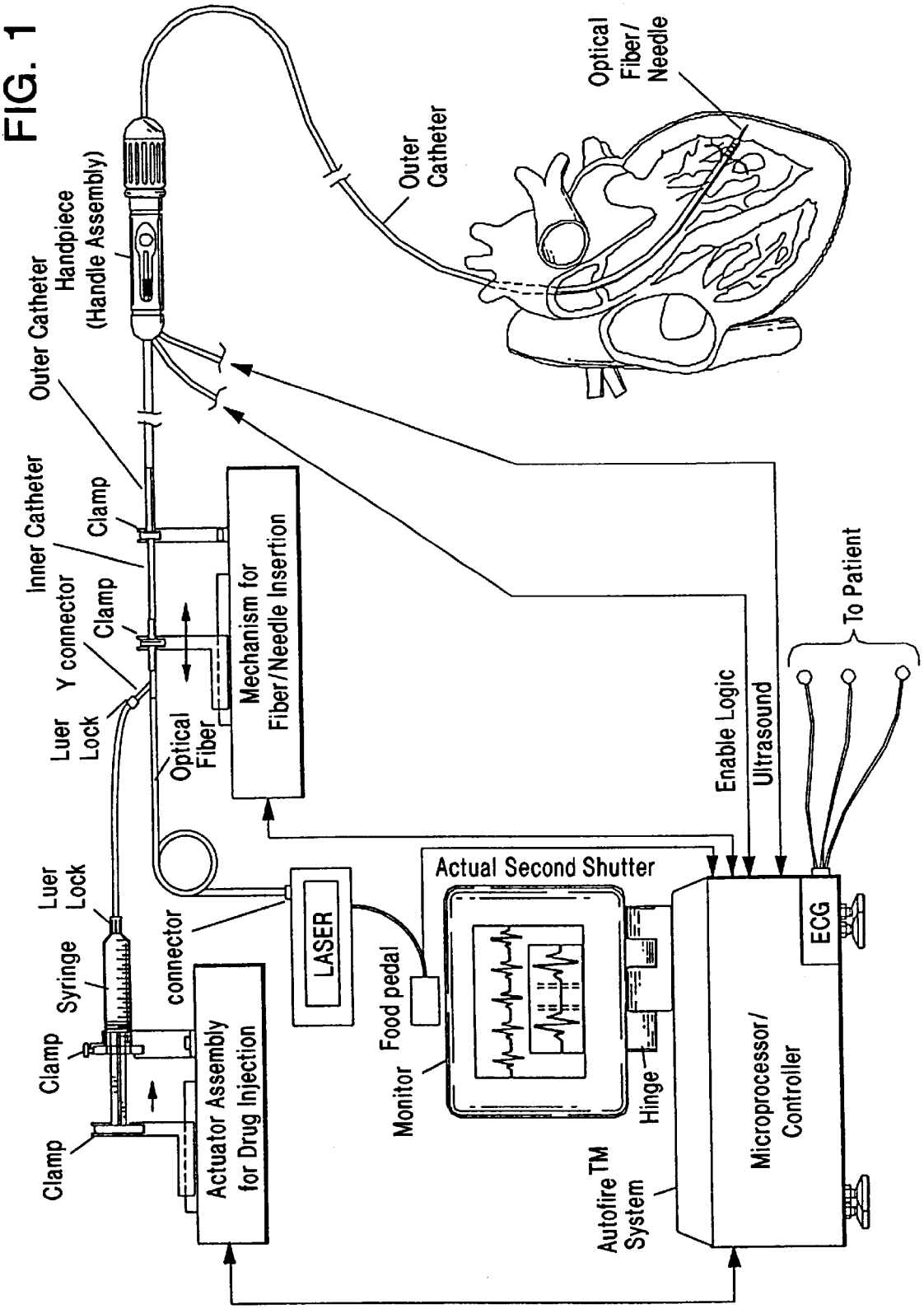
FIG. 1 is a schematic plan view of one embodiment of an apparatus for practicing the methods of the present invention, showing a percutaneous catheter, the distal end portion of which is positioned against the endocardium of the heart, with an inner cannula needle/optical fiber inserted into the myocardium. Also illustrated are one embodiment of the supporting features an apparatus for practicing the methods of the invention may have. The proximal end portion of the outer catheter is removably attached to a housing and the inner catheter/cannula is attached to an actuator, which controls its insertion into and withdrawal from the myocardium. A separate actuator advances the plunger of a syringe for drug delivery during a portion of the inner cannula's insertion into the myocardial wall.

Angiogenic proteins were identified and purified in the 1980's, and found to be mitogenic not only for vascular endothelial cells but also for a wide variety of other types of cells and appeared to promote angiogenesis as part of coordinated tissue growth and repair. Later, the first selective angiogenic growth factor was purified on the basis of its ability to induce transient vascular leakage (vascular permeability factor) and endothelial cell mitogenesis (vascular endothelial growth factor (VEGF) or vasculotropin), subsequent cloning and sequencing of the appropriate genes showed that these two factors were in fact the same, now termed VEGF. See Thomas, K A "Vascular Endothelial Growth Factor, a Potent and Selective Angiogenic Agent" *J. Biol. Chem.* 271(2): 603–606 (1996); Folkman, J and Shing, Y *J. Biol. Chem.* 267:10931–10934 (1992).

The originally characterized form of VEGF (approximately 34–46 kDa) was about 20% identical with platelet derived growth factor (PDGF) A and B chains including conserved CYS residues. Another close homolog called placenta growth factor (P1GF) on the basis of its original source, was also cloned and identified and shares 53% amino acid sequence identity with VEGF. It is thought that VEGF and P1GF may interact in similar fashion as PDGF A and B chains to form hetrodimer proteins.

Acidic and Basic Fibroblast Growth Factor (aFGF and FGF-1 or BFGF) was characterized and compared by Gimenez-Gallego et al., "Brain-derived acidic fibroblast growth factor: complete amino acid sequence and homologies" *Science* 230: 1385–1388 (1985), and has been found to induce angiogenesis. See Thompson et al., Site-directed neovessel formation in vivo" *Science* 241: 1349–1352 (1988); Folkman et al., "Angiogenic Factors" *Science* 235: 442–447 (1987).

Elevated levels of b-FGF have been found associated with patients with unstable angina, however, angiogenesis is believed to require more than just the presence of growth factors; the appropriate receptors must be upregulated and inhibitory factors, such as angiopoetin-II, must be absent. In the heart, angiogenesis may be involved with increased expression of various substances including aFGF, b-FGF, VEGF, PDGF, and others. While some growth factors are constituatively expressed in the myocardium, b-FGF and PDGF are induced by stimulus. It has been found that b-FGF binds to heparin sulfate, which protects the molecule from degradation and allows for storage in the extracellular matrix. Nitric oxide release may also be implicated in the regulation of blood vessel formation.

Hariawala and Sellke "Angiogenesis and the heart: therapeutic implications" *J. R. Soc. Med.* 90: 307–311 (1997) discuss several possible applications of angiogenic factors in treating man. They note that gene therapy using viral vectors appears promising, but that there is the possibility that, after taking up foreign DNA, a normal cell might be transformed to abnormal, with catastrophic results.

Studies have shown that myocardial perfusion can be improved in animal models by continuous administration of angiogenic growth factors. For example, Yanagisawa-Miwa et al., "Salvage of infarcted myocardium by angiogenic action of basic fibroblast growth factor" *Science* 257: 1401–1403 (1992); Harada et al., "Basic fibroblast growth factor improves myocardial function in chronically ischemic porcine hearts" *J. Clin. Invest.* 94: 623–630 (1994); Banai et al., "Angiogenic-induced enhancement of collateral blood flow to ischemic myocardium by vascular endothelial growth factor in dogs" *Circulation* 89,5: 2183–2189 (1994). A recent study attempted to administer a single intraarterial or intravenous bolus of VEGF to treat myocardial ischemia in a porcine heart model. However, in the initial test, half of the test subjects succumbed to severe hypotension following VEGF administration. Hariawala et al., "VEGF Improves Myocardial Blood Flow but Produces EDRF-Mediated Hypotension in Porcine Hearts".

Recently, injection of FGF-1 close to the vessels after the completion of bypass anastomosis was demonstrated to induce neoangiogenesis in human heart. Schumacher et al., "Induction of Neoangiogenesis in Ischemic Myocardium by Human Growth Factors" *Circulation* 97: 645–650 (1998).

Therapeutic Enzymes

It has been widely accepted that thrombolytic agents such as tissue plasminogen activator (tPA) given during the acute phase of MI reduce hospital mortality and improve ventricular function. See The Merck Manual, 16th ed. (Merck & Co., Rahway, N.J., 1990) page 513. Daily systemic administration of a low dose of aspirin (salicylic acid) is now recommended as beneficial for reducing MI due to small thrombosis. Using the apparatus and methods of the invention, genes or vectors encoding for tPA can be injected into the heart of patients to allow their own heart to produce therapeutic levels of tPA. The production of tPA by the heart would allow for immediate and localized thrombolytic activity that would be beneficial in reducing recurrence of MI in high risk patients.

While more patients have been surviving MI due to available intervention and treatments, there has been a subsequent increase in the number of patients suffering from congestive heart failure (CHF), a weakening of the heart muscle. It has been recently reported that gene therapy allowing the heart to produce the enzyme adenylate cyclase (AC) apparently allows the heart to beat stronger, which provides a beneficial therapeutic effect for treating CHF. Gao, M. et al., "Increased expression of adenylylcyclase type VI proportionately increases beta-adrenergic receptor-stimulated production of cAMP in neonatal rat cardiac myocytes", *PNAS(USA)*, 95(3):1038–43; Hammond et al., *American Heart Association Journal (March* 1999). Thus, the device and methods of the invention can be used to inject genes or vectors encoding for AC into the heart of patients to allow their own heart to produce therapeutic levels of AC. The production of AC by the heart would allow for immediate and localized stimulation of cAMP production that would be beneficial in stimulating stronger heart action in patients suffering from CH.

Gene Therapy Vectors

Suitable gene therapy agents and vectors are known and have been described in the art. For example Barr, E, et al. "Efficient catheter-mediated gene transfer into the heart using replication-defective adenovirus" *Gene Therapy* 1:51–58, 1994, gives details on preparation of one example of a suitable virus gene therapy vector and its deleted regions that can be used in conjunction with the device of the invention, along with a CMV cytomegalovirus promoter/enhancer.

Many of the methods and materials useful for carrying out the basic molecular biology manipulations required to construct the appropriate gene therapy expression vectors are known in the art, and can be found in such references as Sambrook et al., *Molecular Cloning*, 2nd edition, Cold Spring Harbor Laboratory Press (1989); Berger et al., *Guide to Molecular Cloning Techniques, Methods in Enymology*, Vol. 152, Academic Press, Inc., (1987); Davis et al., *Basic Methods in Molecular Biology*, Elsevier Science Publishing Co., Inc. (1986); Ausubel et al., *Short Protocols in Molecular Biology*, 2nd ed., John Wiley & Sons, (1992); Goeddel *Gene Expression Technology, Methods in Enzymology*, Vol. 185, Academic Press, Inc., (1991); Guthrie et al., *Guide to Yeast Genetics and Molecular Biology, Methods in Enzymology*, Vol. 194, Academic Press, Inc., (1991); McPherson et al., *PCR Volume* 1, Oxford University Press, (1991); McPherson et al., *PCR Volume* 2, Oxford University Press, (1992); and *Gene Expression Systems*, ed. Fernandez and Hoeffler, Academic Press, (1999).

Preferred Embodiments

The invention teaches a device for creating a pocket within the myocardium of a mammalian heart, said pocket suitable for containing a therapeutic agent deposited within it, said therapeutic agent being either a chemical or molecular biological agent. In a preferred embodiment, the device of the invention encompasses a fiber optic strand, or bundle of strands, located within the lumen of a first catheter such that fluid communication is still possible within the lumen of this first catheter. At the most distal end of this first catheter, the end is so modified as to be made suitable for mechanically puncturing heart muscle. This distal end of the catheter can be attached to a separate puncturing feature that is either a metal cap/tip, or needle. This attachment may be made by means of a flanged coupling and suitable adhesive or mechanical means for attachment. At this distal end of the device, the optical fiber may be fixably attached to the catheter itself, or to the metal tip or needle, or both. When fixably attaching the catheter to the optical fiber and/or needle/tip at this distal end, the attachment is made such that fluid communication is maintained through the lumen of the first catheter and out of the lumen at or near the distal end of the device. The exit may be through the bore of the needle, out exit openings in the end of a metal or plastic tip, or via side ports in the distal end of the needle or tip device. This first catheter, containing the optical fiber within the lumen, may also be suitably used in conjunction with an appropriate outer catheter for manipulation and use in minimally invasive percutaneous or chest endoscopic procedures.

Thus in a particular aspect of the present invention, the invention encompasses a distal end needle/tip-optical fiber construct which provides for fluid communication through openings in the tip to the lumen of a first catheter, while allowing for a fixed attachment of the distal end of an optical fiber, or bundle of fibers within said tip.

Implementation of the procedures of the present invention by the operation of certain exemplary device embodiments suitable for practicing the method of the invention is further described below.

In a first embodiment, for performing a percutaneous gene therapy procedure, the distal end of an optical fiber, whose distal end is encased in a short length of syringe needle and whose proximal end is optically coupled to a source of laser energy, is contained within an inner catheter in fluid communication with the space between the optical fiber and the attached needle. The fiber/needle inner catheter may also be movably disposed within a flexible outer catheter. The distal end of the outer catheter is placed against the endocardium of a heart after advancement via the vasculature into a heart chamber, which outer catheter may optionally provide for temporary mechanical anchorage means to counter the force of insertion of the needle/fiber into the heart wall. The needle/optical fiber is advanced a first predetermined distance into the heart wall. The needle advances a second, predetermined distance while emitting laser energy, creating a pocket within the heart muscle. As the needle is being withdrawn, the second predetermined distance, a therapeutic fluid is injected into the pocket, after which the needle withdraws the first selected distance out of the tissue. The therapeutic agent is trapped in and remains substantially within the pocket, immediately after administration.

During an open chest or endoscopic myocardial gene therapy procedure, the optical fiber/needle/inner catheter assembly is movably disposed within a handpiece terminating in a metal cannula whose distal end has a metal flange or collar. The collar is placed against the epicardium surface of a heart. The needle/optical fiber is then mechanically advanced a first predetermined distance into the heart wall. The needle/fiber advances a second predetermined distance while emitting laser energy, creating a pocket in the myocardium. Injection of a therapeutic agent occurs as the needle/fiber withdraws the second selected distance, and the needle/fiber then withdraws the first selected distance from the heart wall. The agent remains trapped within the pocket in the heart wall.

In a preferred embodiment, the method of the invention is practiced on a beating heart with synchronization of the movement of the apparatus being timed to begin at a selected time after the "r" wave of the patient's electrocardiogram (ECG) and to conclude within diastole, when the heart's electrical activity is minimal and the risk of an arrhythmia is least. In both procedures, the needle/tip insertion distance and operation of the device can be armed by the surgeon by pressing a button or controlled by automatic activation after abutment of the needle/fiber tip to the surface of the heart. Activation of the device occurs a selected time after the "r" wave of the patient's ECG. Automation can control the stepper motor mechanism for partially advancing the needle/tip, advancing the needle/tip an additional distance while emitting laser energy, injecting a selected amount of agent as the needle/tip is being partially withdrawn, and completing the withdrawal of the needle/tip from the heart wall.

If the heart is arrested, the device can be activated by pressing a button or by abutment of the device against the heart, depressing a lever or actuator.

The various features and embodiments of the claimed invention are further illustrated by the description of the preferred embodiments below.

One example of a device suitable for practice of this embodiment of the invention is illustrated in FIG. 1. A catheter for insertion into the femoral artery could contain, in addition to a handpiece containing an activation button, about 20 to 90 cm from its distal end, a mechanism and wires to articulate the distal end of the flexible outer catheter, which defines a channel to accommodate the fiber/needle assembly encased in an inner catheter.

As seen in FIG. 1 (and FIG. 7) a microprocessor controller monitors the patient's ECG and, at the times in the cardiac cycle selected by the operator, signals the advancement/withdrawal mechanism to move the fiber/needle assembly, fire the laser, signal the fluid injector to inject fluid as the needle is being withdrawn and completing the withdrawal of the fiber/needle.

Figure 2B:
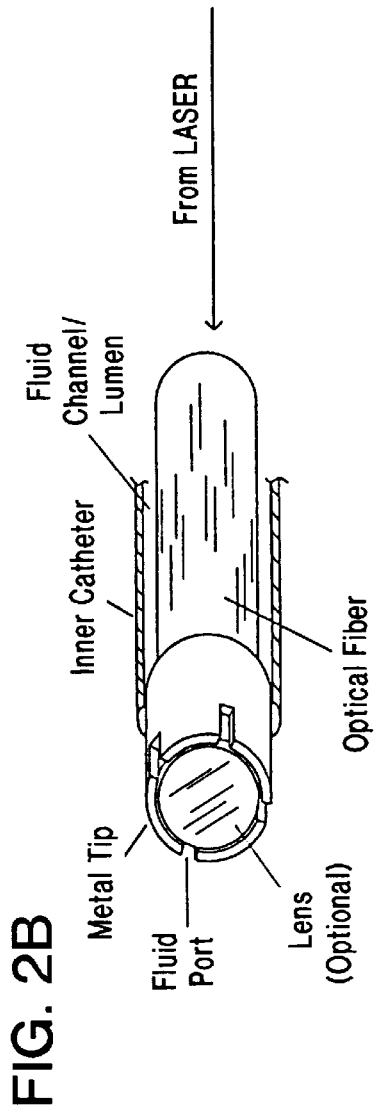
FIG. 2B is a partial cutaway sectional view of one embodiment of an optical fiber/inner catheter device for practicing the methods of the invention (the positioning of an optical fiber within the lumen of the movable inner cannula is shown with the inner catheter being cut-away). In this particular embodiment, a metal tip which can be crimped down to firmly attached to the optical fiber is shown. This tip is shown as blunt ended, but may be beveled to create a sharper puncturing tip. As shown in all figures, the single optical fiber may also be a suitable bundle of smaller diameter optical fibers.
Figure 2C:
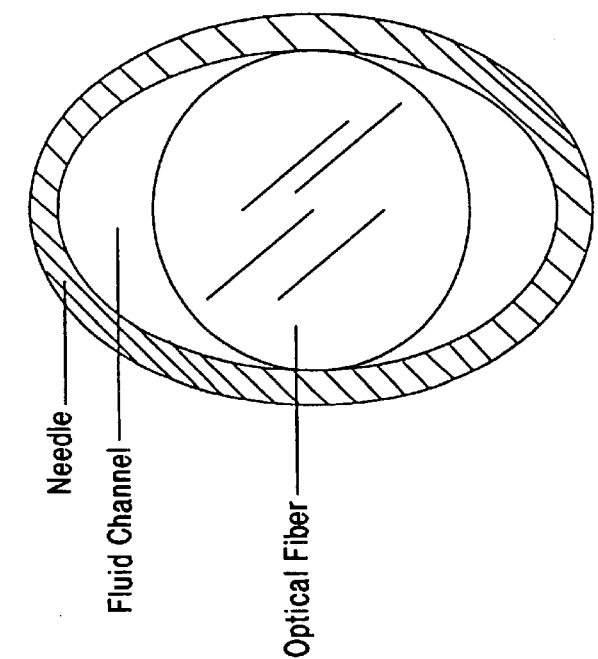
FIG. 2C is a cross-sectional view of a needle/optical fiber device of the invention, wherein the needle is crimped so as to firmly fix the optical fiber within the bore of the needle, allowing fluid communication via the remaining space of the bore.

Optionally, as shown in FIG. 2A, instead of a short length of syringe needle affixed to the distal end of the optical fiber, a metal tip, containing a lens to expand the beam and one or more fluid ports, could be attached by crimping to the distal end of the fiber in fluid communication with the inner catheter. For example, a lens to expand the beam could be fitted over the optical fiber at the distal end of the metal (or plastic) tip shown in FIG. 2B. As seen in FIG. 2B, a lens is contained in a metal tip, crimped to the optical fiber as shown in FIG. 2C, with fluid communication channels between the lumen and the fluid posts in the metal tip. The device of FIG. 2B is described in U.S. Pat. No. 4,773,413 to Hussein et al., and incorporated herein by reference. The lens diverges the beam to make a pocket of a larger diameter.

Figure 3:
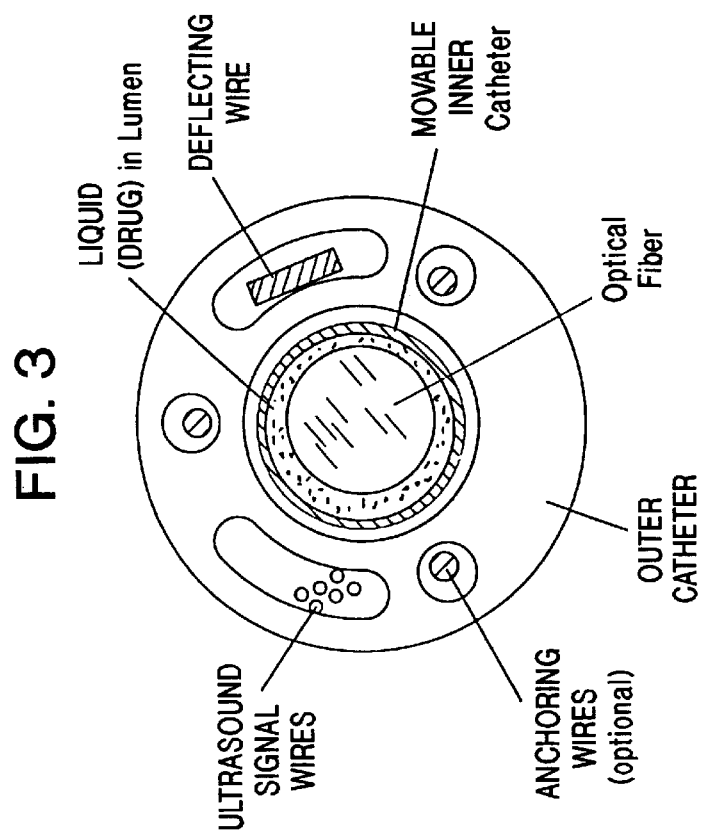
FIG. 3 is a cross sectional view taken along line 3—3 shown in FIG. 2A, showing a cross section of one embodiment of the outer catheter with an inner movable catheter through which liquid drug or other therapeutics can be delivered to the site of pocket formation, and the optical fiber positioned within this inner catheter. Also shown are optional anchoring wires and optional ultrasound signal wires.

As seen in FIG. 3, the outer catheter may contain several channels, in addition to a central channel through which the optical fiber/needle/inner catheter assembly may be advanced and withdrawn. One channel contains a deflecting wire for manipulating the distal end of the outer catheter. Additional channels may optionally contain anchoring wires, and may also contain wires to an ultrasound transducer in the distal end of the outer catheter, enabling the operator to determine the thickness of the heart wall at the point of the outer catheter in contact with the heart.

Figure 4:
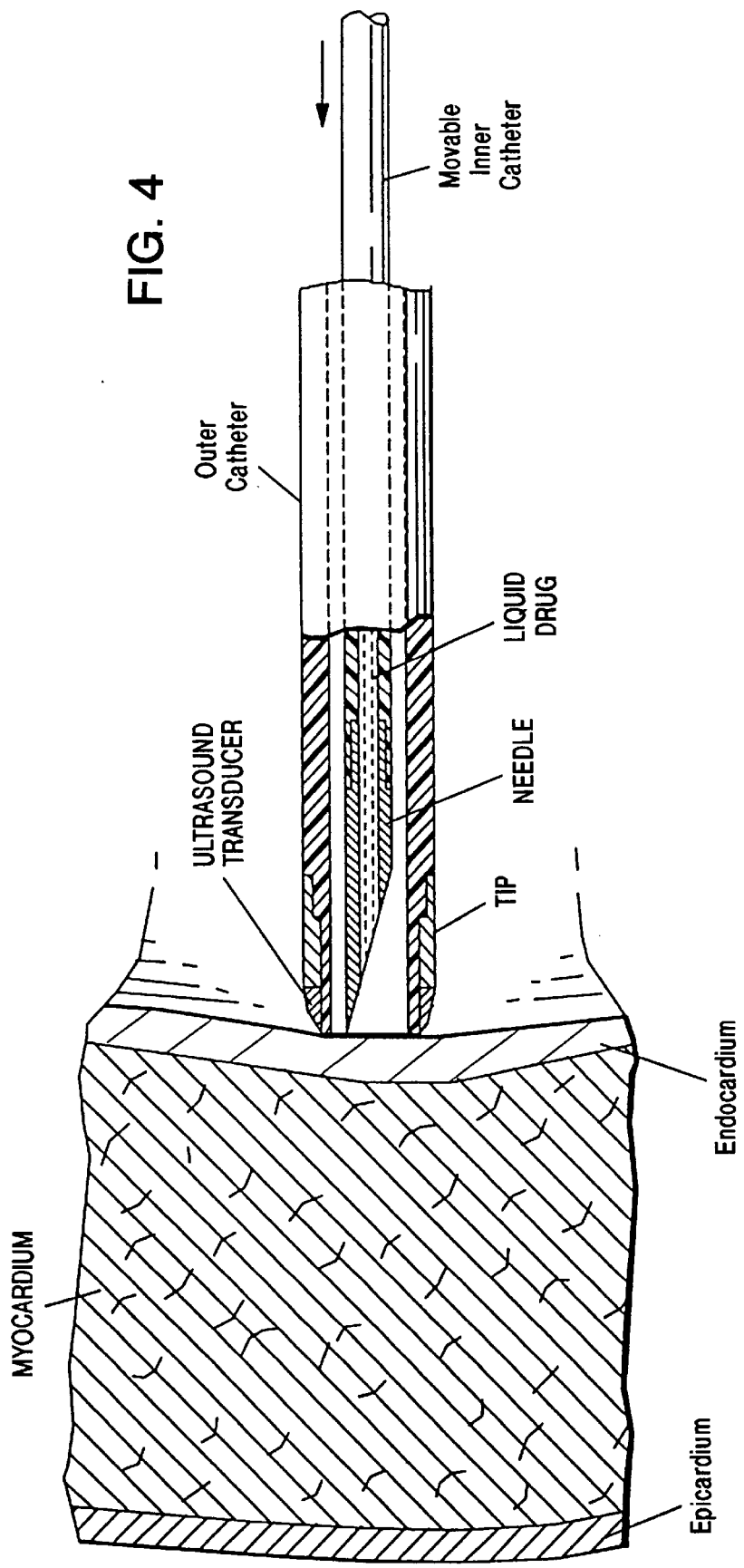
FIG. 4 is a cutaway cross sectional view of the distal end portion of one percutaneous catheter suitable for practicing the methods of the invention, showing the tip positioned against the endocardium (for simplicity, the positioning of an optical fiber within the lumen of the movable inner cannula is not shown).
Figure 5:
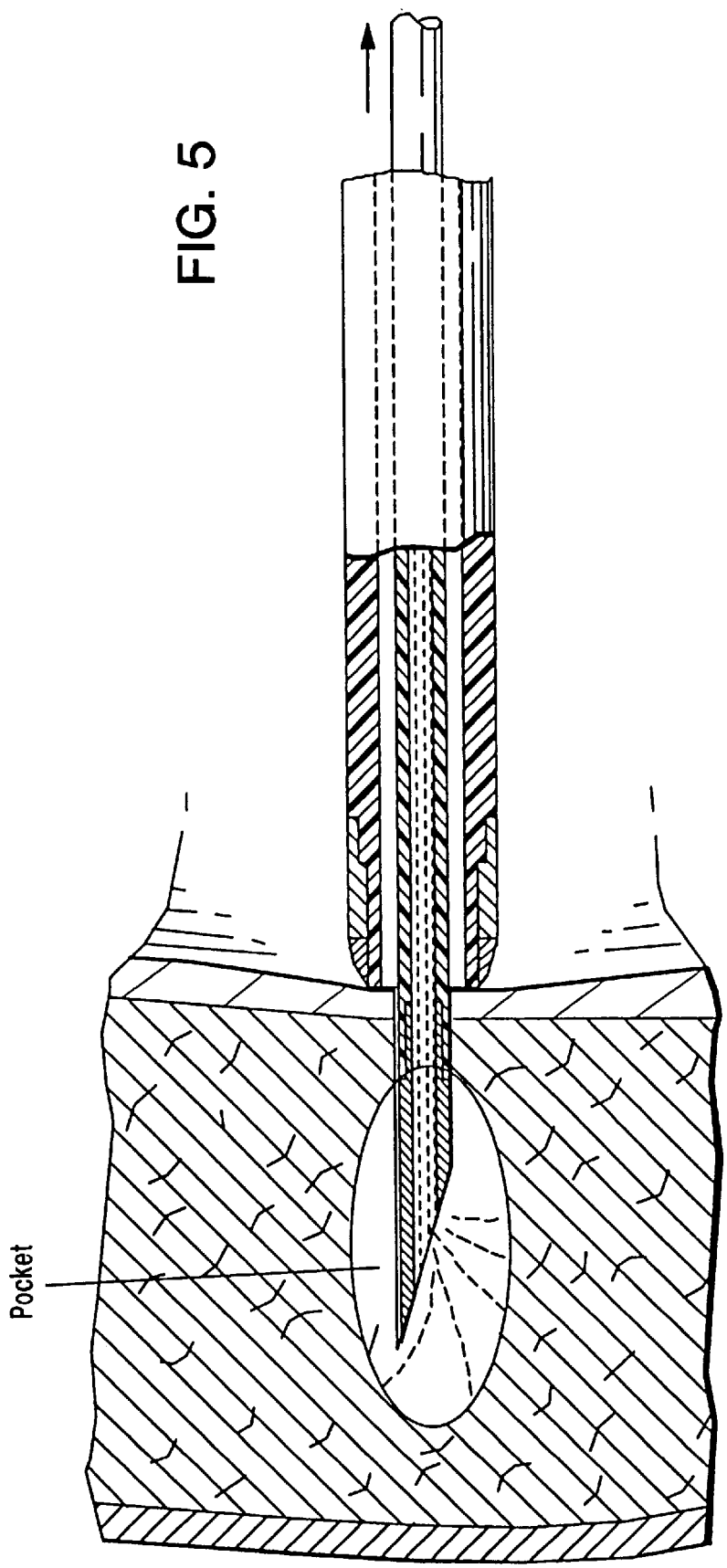
FIG. 5 is similar to that of FIG. 4 except the inner cannula needle/optical fiber assembly has been advanced and inserted into the myocardium, and a pocket formed by laser energy from the optical fiber (not shown), with the liquid drug or therapeutic being injected into the pocket formed therein the heart muscle as the needle/optical fiber assembly is being withdrawn (for simplicity, the positioning of an optical fiber within the lumen of the movable inner cannula is not shown).

In FIG. 4, the distal end of the outer catheter is positioned against the inner surface of the heart wall (endocardium). In FIG. 5, after mechanical insertion into the heart muscle, and advancement into the myocardium while emitting laser energy creating a pocket, a therapeutic agent is injected as the needle assembly is being withdrawn from the pocket.

The preferred method of the present invention, either percutaneous or via epicardial insertion, calls for the partial insertion of the needle/fiber device 25% to 40% of the thickness of the heart wall by mechanical energy. The needle/tip may be small in diameter, about 14 gauge to 20 gauge, preferably 16 to 18 gauge, thus creating a small puncture wound which will be easily clotted or otherwise closed. As the needle/fiber device is advanced another 25% to 40% of the heart wall thickness, laser energy is emitted to create a pocket within the heart wall. As the fiber/needle device withdraws the second 24% to 40% of the heart wall thickness, injection of therapeutic liquid, containing a drug or other therapeutic contents, into the pocket is effected. While the injection of liquid preferably occurs in conjunction with the withdrawal of the needle/fiber tip, it can occur with the tip stationary. Injection of fluid is preferably via the space between the needle and the optical fiber by way of the inner catheter, which is in fluid communication with the needle tip. The fluid may enter the inner channel via a tube from an external fluid source.

Figure 6:
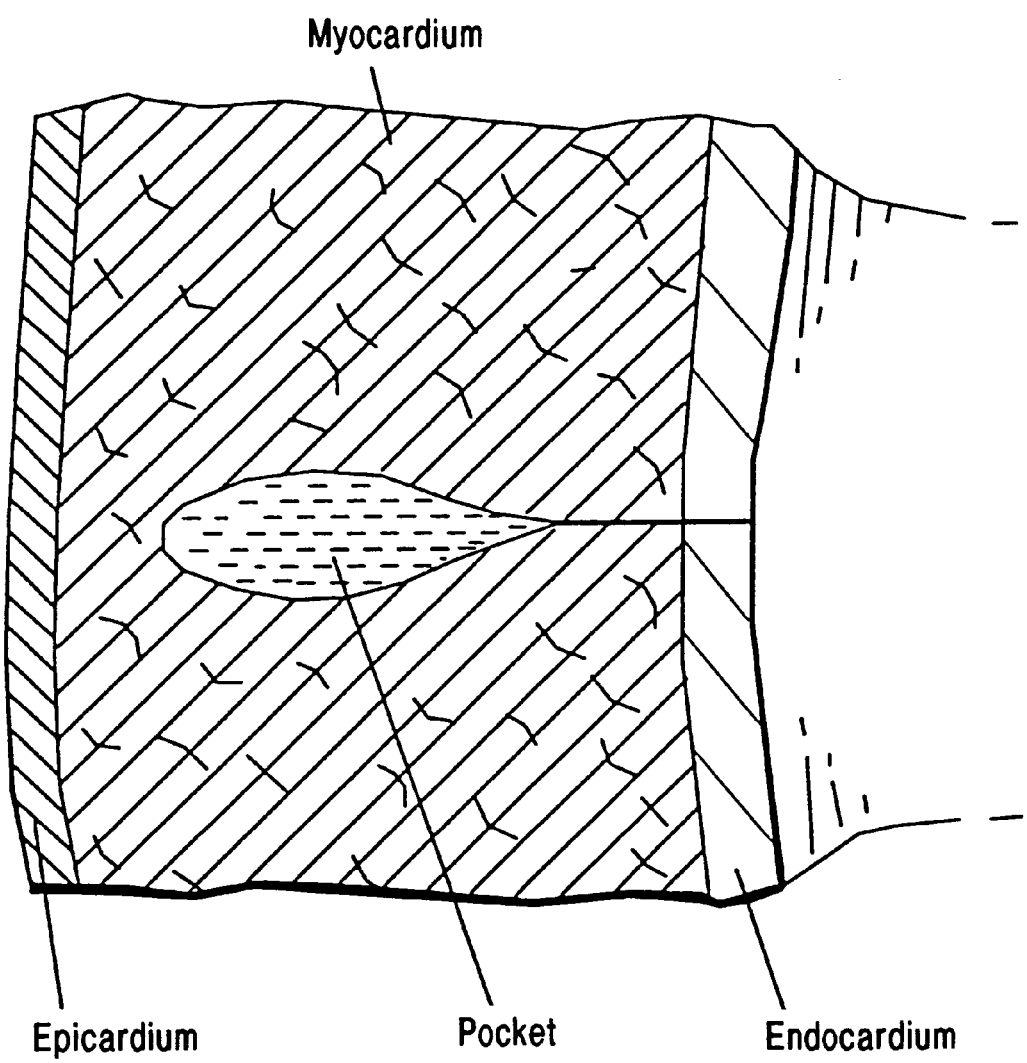
FIG. 6 is a cross sectional view of a heart wall, showing the pocket of drug within the myocardium created after injection from within the heart during a percutaneous procedure.

FIG. 6 is a drawing illustrating the resultant pocket formation containing the therapeutic agent in the myocardium after percutaneous treatment from the inside or endocardial surface of the heart wall. The tissue effect of performing the procedure from the outside or epicardial surface through the chest wall, is similar to that done percutaneously, however the wound is oriented in the opposite direction, originating from outside the heart. Because of the needle leaves only a needle puncture in the epicardium, which quickly clots or seals, bleeding is minimal.

As described above, once the needle has penetrated to a first desired depth through the endocardium and into the heart muscle wall, an actuator means can trigger the emission of laser energy from the optical fiber while the needle is advancing a second additional distance through the myocardium of the heart, causing the formation of a pocket within the heart wall. Once the needle and the fiber have created the desired pocket into the heart wall, the transmission of laser energy within the fiber is terminated. Once the pocket is formed, liquid drug or therapeutic can be administered via the lumen of the inner cannula through the needle into the just formed pocket, as the fiber needle withdraws from the pocket. Once fully injected with drug or therapeutic, the fiber and the needle are fully removed from the tissue.

Figure 7A:
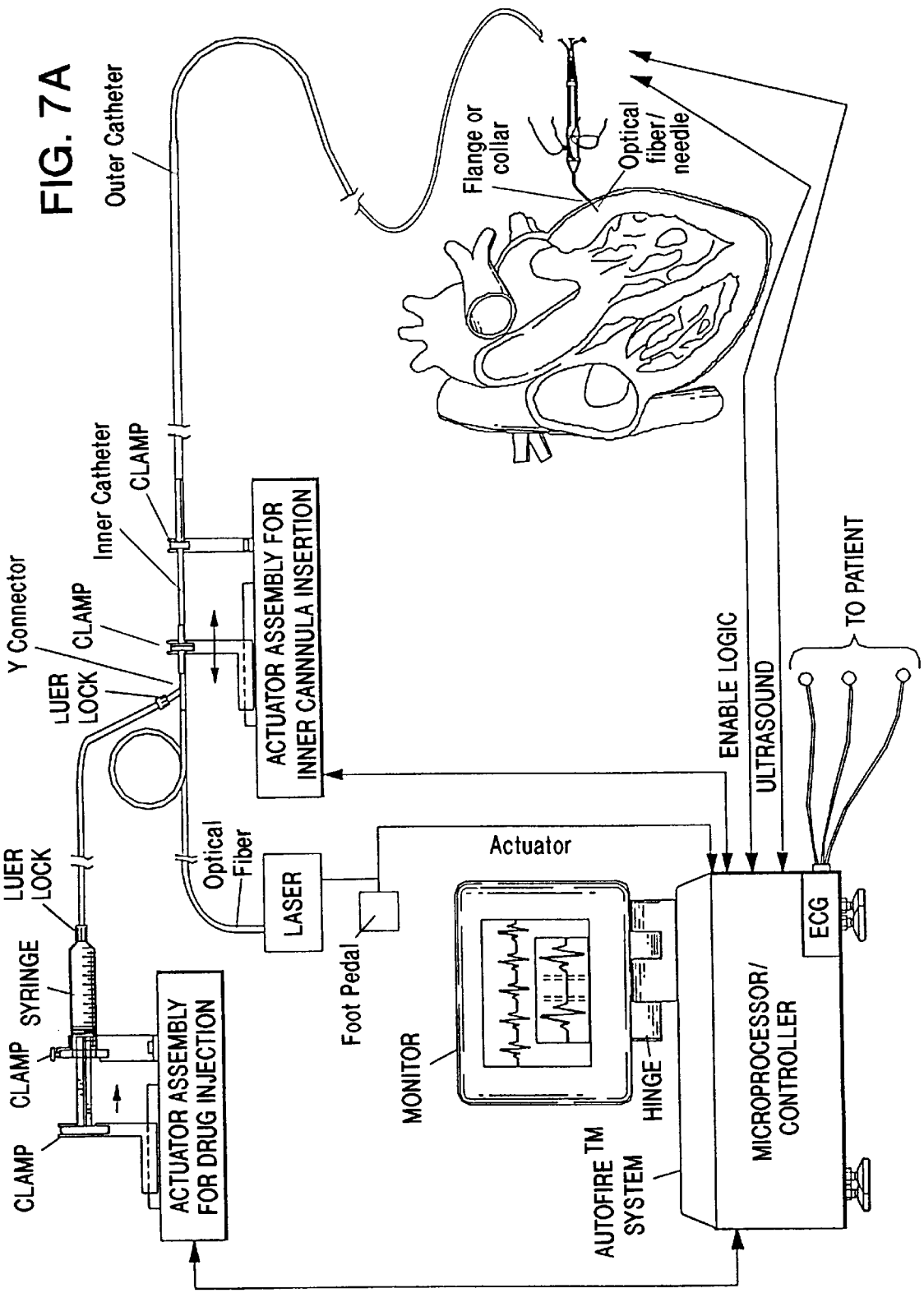
FIG. 7A is a schematic plan view, similar to that of FIG. 1, of one embodiment of an apparatus for practicing the methods of the present invention, showing a handpiece and catheter for use in an open heart or endoscopic procedure, the distal end portion of which is positioned against the epicardium of the heart, with an inner cannula needle/optical fiber inserted into the myocardium. Also illustrated are one embodiment of the supporting features an apparatus for practicing the methods of the invention may have. The proximal end portion of the outer catheter is removably attached to a housing and the inner catheter/cannula is attached to an actuator, which controls its insertion into and withdrawal from the myocardium. A separate actuator advances the plunger of a syringe for drug delivery during a portion of the inner cannula's insertion into the myocardial wall. For a endoscopic procedure, the distance between the needle/optical fiber and handpiece can be greater than that depicted.

In one embodiment of an apparatus for performing an epicardial treatment, during an open chest operation or through a puncture between the ribs, with an endoscope (thoracoscope) through a second puncture for visualization, as seen in FIG. 7A, the distal end of the cannula attached to an actuator handpiece is pressed against the surface of the heart (for example the left ventricle) by the surgeon. By manually activating the actuator, the needle/optical fiber assembly is first mechanically inserted 24% to 40% of the heart wall thickness into the heart muscle. Laser energy is emitted as the optical fiber/needle energy advances a second 24% to 40% thickness of the heart wall. The emission of laser energy ceases and, as the needle is withdrawn the second 25% to 40% of the thickness of the heart wall, a drug is released into the pocket formed in the heart wall as shown in FIG. 7B. The needle/fiber assembly is then withdrawn from the heart wall. In similar fashion to the operation of the needle/optical fiber of a percutaneous device, the insertion of the needle/optical fiber into the heart muscle does not penetrate completely through the heart wall and results in the formation of a pocket within the heart wall. In this case, the drug can be injected into the pocket, concurrent with, or after partial withdrawal of the needle/optical fiber from the pocket, but before complete withdrawal from the heart wall. Once the needle/optical fiber device is completely withdrawn from the heart, the wound will either clot or seal to retain the injected drug or therapeutic inside the pocket formed in the heart muscle wall (FIG. 13C).

Figure 7C:
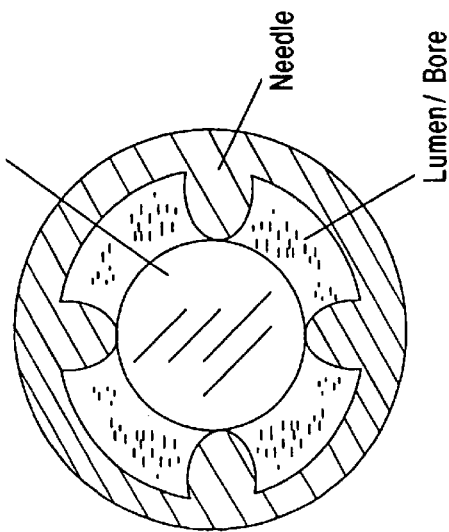
FIG. 7C is a cross-sectional view of one embodiment of an optical fiber/needle for practicing the invention, wherein the needle is designed with ribbing within the bore of the needle to firmly grasp the optical fiber when it is placed within this bore. Such ribbing can be straight, or spirally disposed.
Figure 7B:
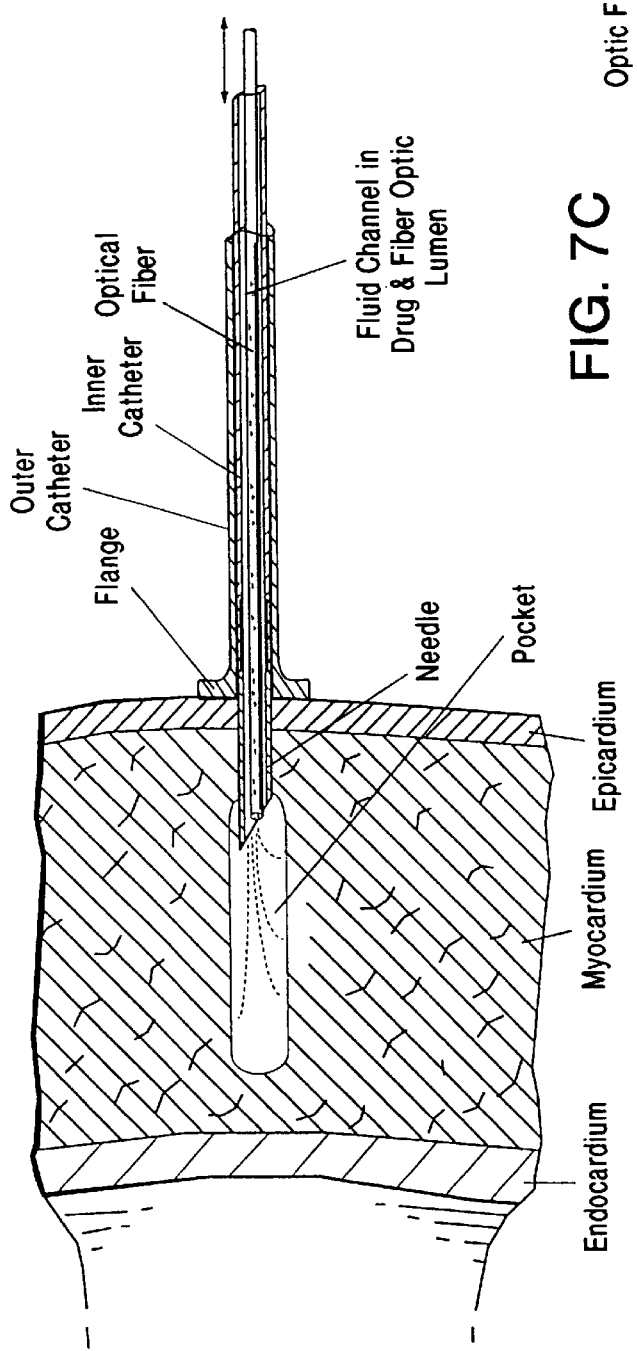
FIG. 7B illustrates the insertion of a needle/optic fiber device for practicing the methods of the invention by open heart or endoscopic procedure between the ribs, depicting the abutment of a flange against the epicardium and the injection of liquid drug or therapeutic into the heart muscle pocket formed by the laser energy through the optical fiber into the myocardium of the heart (here the optical fiber is shown within the lumen of the inner catheter, which is movably disposed within an outer cannula/catheter).
Figure 8:
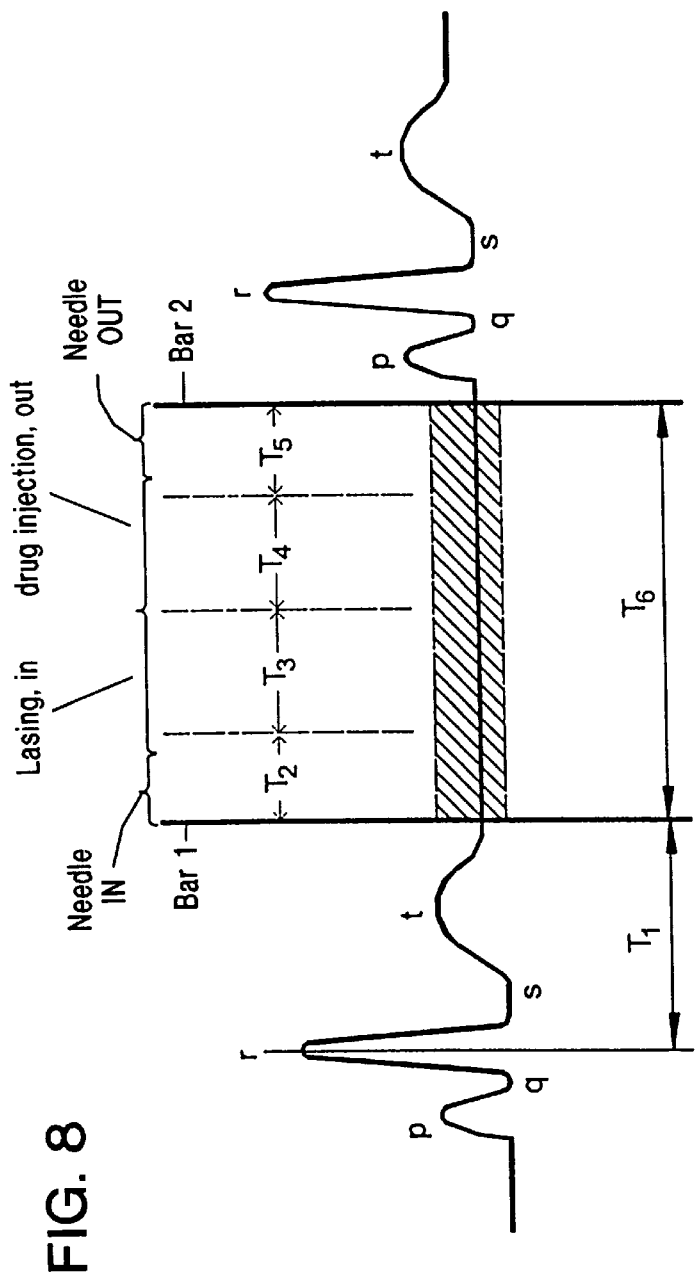
FIG. 8 is a diagram, showing a typical ECG wave form of a patient, upon which the window of time between heart beats for insertion of the inner cannula needle into the myocardium and injection of drug is defined by the operator locating Bar 1 and Bar 2. The mechanical insertion, advancement while lasing, and drug injection into the myocardial wall during withdrawal, and withdrawal from the heart wall is shown and are timed such that the procedures of the invention are synchronized from the "r" wave of the patient's ECG to fall within diastole.

As seen in FIG. 7C, in this embodiment, the needle is crimped to the optical fiber and fluid channels are created by either creating troughs in the inner wall of the needle or in the buffer coating of the optical fiber. The procedures of the invention can be accomplished on a beating heart, synchronized with the heart beat and preferably a predetermined period of time after the "r" wave of the patient's ECG, during diastole. Once the proper synchronization is obtained, activation of the device can be manual, or automatically triggered by the monitoring device, to effect insertion, lasing, injection and withdrawal, all within the course of diastole, through the surface of the heart. As with the percutaneous apparatus and treatment, he preferred timing of treatment is shown in FIG. 8.

If used in an endoscopic procedure, the flange on the metal cannula should be approximately 4 to 6 mm in diameter, enabling it to be inserted through a small bore trocar puncture between the patient's ribs.

The apparatus for performing the procedure on an arrested heart during coronary bypass surgery or other open chest procedure is similar to that described above, except activation of the device is by pressing a button on a handpiece, or by depressing an actuator lever when the distal end of the metal cannula is pressed against the heart wall.

For an epicardial device, it is preferred that the needle or tip (either metal or plastic) be a 14-gauge to 20-gauge size, preferably 16 to 18 gauge, with a single 300 to 1000 micron diameter optical fiber, or a bundle of 50 to 100 micron core diameter optical fibers therewithin. Typically, a 14-gauge needle or tip will have a 1000 micron core diameter or smaller optical fiber therewithin, and a 16 or 18-gauge needle or tip will have a 500 to 600 micron core diameter or smaller optical fiber therewithin. For an endocardial device, the needle/tip can be 18 to 20 gauge with a 365 micron core diameter or smaller optical fiber, or a bundle of 50 to 100 micron core diameter optical fibers therewithin.

Timing of Administration

Beating Heart

When the methods of the invention are used to treat a beating heart, assuming a beating heart rate of 60 beats per minute, it is desired that the above procedures take only about 0.2 to 0.6 seconds, preferably 0.3 to 0.5 seconds, from the time the fiber/needle begins to extend from the device, the pocket is formed, the therapeutic agent administered, and the fiber/needle is fully retracted back into the device. If the heart rate is higher than 60 beats per minute, the above times would be proportionally shorter. The above procedure may be conducted over a longer period of time in an arrested or slowed heart, for example, during coronary bypass graft surgery, or in a beating heart over a period of several beats, if desired, for example, when a lower powered laser is to be used, which cannot make the pocket in 100 to 150 msec. In any case, advancing the device mechanically at a selected rate of speed at a desired energy level enables the channels to be made with a uniform diameter and depth of coagulation zone surrounding the channel.

It should be noted with regard to all of the embodiments depicted above that the laser can be activated by a foot-pedal, finger-button, activator rod or by a control unit's sensing the "r" wave of the patient's ECG and supplying an activation signal to the laser or a movable mirror which will divert or enable laser energy to enter into the optical fiber. Likewise, the movement of the arm of the advancement mechanism can be activated by a foot-pedal, finger-button, activator rod or a control system which senses the "r" wave of the patient's ECG.

It is preferred that a control unit monitor the heart by a conventional ECG sensing means to control the operation of the device by using a signal recognition and timing procedure similar to that disclosed by U.S. Pat. No. 4,788,975, issued to Shturman et al., and incorporated herein by reference.

Preferably, the device enters the heart wall, forms a pocket within the heart wall by emission of laser energy, injects a therapeutic agent and withdraws from the heart wall during diastole, as shown in FIG. 8. It is desired that the control unit determine when to form the pocket in the heart by interposing an appropriate delay time from the "r" wave of the patient's ECG, taking care to avoid activation of the device in the event of a premature ventricular contraction or any other unusual variation in heart rhythm.

Forming the pocket when the heart is in diastole is preferred because, at that moment, the electrical activity of the heart is least affected by the trauma of the entry of the needle and the emission of laser energy. Also, the heart chamber is full of blood and the heart wall is at its thinnest.

As used in FIG. 8, T1 is the time delay from the "r" wave of the patient's ECG to the inception of movement of the fiber/needle assembly into the heart wall from either the epicardial or endocardial surface. T1 should extend from the "r" wave to the trailing edge of the "t" wave.

T2 is the time during which the fiber/needle advances the first selected distance into the heart wall, approximately 50 to 100 milliseconds.

T3 is the time during which laser energy is emitted as the fiber/needle advances the second selected distance into the heart wall and momentarily stops (laser energy ceases), approximately 50 to 100 milliseconds.

T4 is the time during which, as the fiber/needle withdraws the second selected distance from the heart wall, the therapeutic agent is injected, approximately 50 to 100 milliseconds.

T5 is the time during which the fiber/needle withdraws the first selected distance from the heart wall, approximately 50 to 100 milliseconds.

In a preferred embodiment, the patient's ECG is displayed on a control unit, and a single heart cycle can be displayed thereon. The operator can move a Bar 1 by touching a left or right icon on a touch screen or similar device to set the position of Bar 1 in relation to the displayed ECG. Similarly, the operator can move and set Bar 2 by touching a left or right icon on a touchscreen or similar device.

When Bar 1 and Bar 2 have been properly positioned on the patient's ECG, the control unit senses the "r" waves, computes the "r" to "r" heart rate, takes into account the numbers the operator has input for desired distance of penetration into the heart wall, and distance without lasing, and instructs the stepper motor of the fiber advancement mechanism to commence its advancement and withdrawal at the proper time at the a speed necessary to complete the total travel distance in T6, the time period selected by positioning Bars 1 and 2. In addition, at the proper time, the control unit also signals a shutter mechanism in the control unit or, alternatively, in the laser, to open and close at the beginning and end of T2, and the control unit signals the stepper motor of the syringe injection mechanism to inject the therapeutic agent during T4.

T1, 2, 3, 4, 5 and 6 can be displayed numerically, and Bars 1 and 2, T1, 2, 3 and 4 can be displayed graphically in distinctive bars or stripes on the display/monitor.

In a procedure where the heart has been arrested, the device may be used with a Holmium:YAG laser or, preferably, with an excimer laser for controllably emitting substantially non-thermal laser energy from the distal end of the fiber. However, excimer lasers are of limited power and generally take 5 or more seconds to make a 4–5 mm pocket in the heart wall. In a procedure where the heart is beating, a laser generating a greater amount of energy, such as a Holmium:YAG laser, is desired.

Before use, the laser is set to deliver a desired amount of energy. The laser is enabled to generate laser energy by depressing a footswitch or the like. Activation, insertion, lasing, injection and withdrawal are not critically linked to any specific timing with the heart arrested. However, it is preferred to perform each procedure in the same period of time at the same energy level to assure uniformity of the pockets and the coagulation zone, as well as to minimize the time during which the heart is arrested, and to perform the procedure efficiently using a suitable device.

As known by those skilled in the art, conventional holmium lasers have a "ramp-up" time of up to 1 second or longer from the time the laser medium is stimulated to produce laser energy until the time when laser energy is actually provided. Since it is desired that the device be used with any conventional holmium laser during surgery, an optical fiber can convey laser energy from a laser into a controller, which contains an optical coupler and a separate shutter mechanism. The actuator (ie. foot pedal) of the laser is depressed and laser energy is transmitted to the closed shutter in the controller. When the fiber/needle has advanced to the point where the emission of laser energy is desired to create the pocket, the shutter in the controller opens, and laser energy is transmitted through the optical fiber/needle.

Alternatively, the controller can be connected by one or more wires to the CPU (computer processing unit) or the final (second) shutter mechanism of the laser, taking-over its operation. Instead of opening the final shutter of the laser when the foot pedal is depressed, the final shutter remains closed and laser energy is emitted into it. When the control unit sends a signal to the laser the shutter opens, laser energy is emitted into the optical fiber, and the shutter closes at the desired moment. This, however, requires wiring the laser, and it may not be practical to wire all types of lasers in the market, and their warranty may be invalidated by doing so.

If laser energy is emitted at about 3 Joules per pulse at a repetition rate of about 26 Hertz, for a 50 to 100 millisecond lasing period, approximately $\frac{1}{20}$ to $\frac{1}{11}$ of 26 or approximately 1 to 3 pulses (3 to 9 Joules) would be emitted, sufficient to make an approximately 1 mm diameter channel about 2 to 4 mm in length. Since Holmium laser pulsed energy will create lateral fractures or fissures in the tissue, a void greater than about 2 to 4 cubic millimeters results. Since only about 0.025 to 0.2 cc of liquid containing a therapeutic agent (i.e. an angiogenic growth factor or virally-linked angiogenic gene construct), preferably about 0.05 to 0.1 cc of fluid, is needed to deliver therapeutic agents to the heart, the space created would be adequate to hold this volume of fluid. For example, an angiogenic gene construct, containing $1 \times 10^7$ to $2 \times 10^{11}$ pfu of virus linked to an angiogenic gene, preferably about $1 \times 10^9$ to $2 \times 10^{10}$ pfu of the same, optionally along with angioprotein-1 or other substances, could be contained in 0.05 to 0.1 cc of fluid.

Ultrasound Guidance

In all of the disclosed devices for practicing the various embodiments of the invention, ultrasound imaging may be used to assist the surgeon in determining the thickness of the heart wall. A conventional ultrasound procedure, may be conducted before the procedure, with the physician preparing a chart or remembering from the ultrasound image the thickness of the heart wall at various places, or ultrasound imaging may be performed during the procedure, with the physician or an assistant periodically observing the ultrasound image display and determining the heart wall thickness.

Optionally, an ultrasound emitting and receiving probe may be incorporated in the distal end of the needle/fiber collar of the epicardial device or the distal end of the endocardial device, or on a separate hand held device. The ultrasound image may be displayed on a TV monitor, so that the surgeon or an assistant can visualize the thickness of the heart wall at the point where the optical fiber is to penetrate the heart wall. In addition, the emission of laser energy into the heart causes steam bubbles, from the absorption of laser energy by blood in the tissue. These bubbles can be visualized to confirm that the pocket was formed.

In another embodiment, the aforesaid ultrasound emitter/receiver may also transmit image data to a microcontroller, which processes the data, calculate and display the thickness of the heart wall. The microcontroller can also compute and operate the fiber/needle advancement and drug injection mechanisms, such that the needle is advanced, the pocket is created by the emission of laser energy, the agent is injected and the needle is withdrawn the desired distances, based on pre-selected instructions.

Furthermore, with regard to all of the devices described, as the needle is advanced into the heart wall while the laser is firing, a plasma of hot gasses from the vaporization of tissue forms ahead of the needle and/or fiber. These hot gasses cannot escape backwards, as the tissue hugs the needle in the channel, and solid tissue remains ahead of fiber and/or needle. These hot gasses accumulate and cause the diameter of the channel to increase as the fiber and/or needle advance through the myocardium, which may result in a larger ultimate channel in the middle area of the heart wall. However, to limit the zone of coagulation about the channel and lateral damage to the myocardium, it may be necessary to advance the fiber/needle at a relatively fast rate for a very short time and a given energy level to achieve a desirable and uniform channel diameter, pocket size, and coagulation zone.

Laser Source

Laser sources suitable for adaptation to the methods of the present invention, and use of the device of the present invention are described in the art. In a preferred embodiment, the laser device produces energy from a Holmium:YAG laser or comparable laser at a wavelength of 1400 to 2200 micrometers. Energy from an excimer laser (300 to 400 micrometers), argon laser (488–520 micrometers), KTP laser (532 micrometers), erbium laser (2940 micrometers), or any other source of laser energy able to be transmitted through optical fibers, pulsed, gated, or continuous wave may be utilized. Preferably, a mutli-head Holmium laser, as described in U.S. Pat. No. 5,242,438 to Saadatmanesh et al., is preferred.

Needle/Tip-Optical Fiber/Inner Catheter Assembly

In one embodiment, a simple device for penetrating tissue mechanically using a syringe needle in which an optical fiber is encased, for the application of laser energy after the device has first penetrated a selected distance into the tissue has been designed.

Since the length of the needle must sometimes be limited, when for example, the fiber must be bent at a sharp angle to pass through a canula or to articulate in a desired direction in a confined space, for example in the left ventricle of the heart, the needle must be firmly anchored to the optical fiber. Otherwise, the needle will not advance in synchrony with the optical fiber, or the needle can become detached.

The device of the invention solves this problem by crimping the needle to the optical fiber at about the 9 and 3 clock positions (when looking in cross-section), resulting in an oval shape with fluid conveying channels at about the 12 and 6 clock positions, as shown in FIG. 2C.

The needle/optical fiber tip will comprise, in one embodiment, an optical fiber extending through the inner cannula where about 6 to 15 mm of the distal end of the optical fiber is encased within an appropriate length of syringe needle (preferably about 8 to 12 mm), preferably with a sharp, double-beveled distal end.

Figure 9:
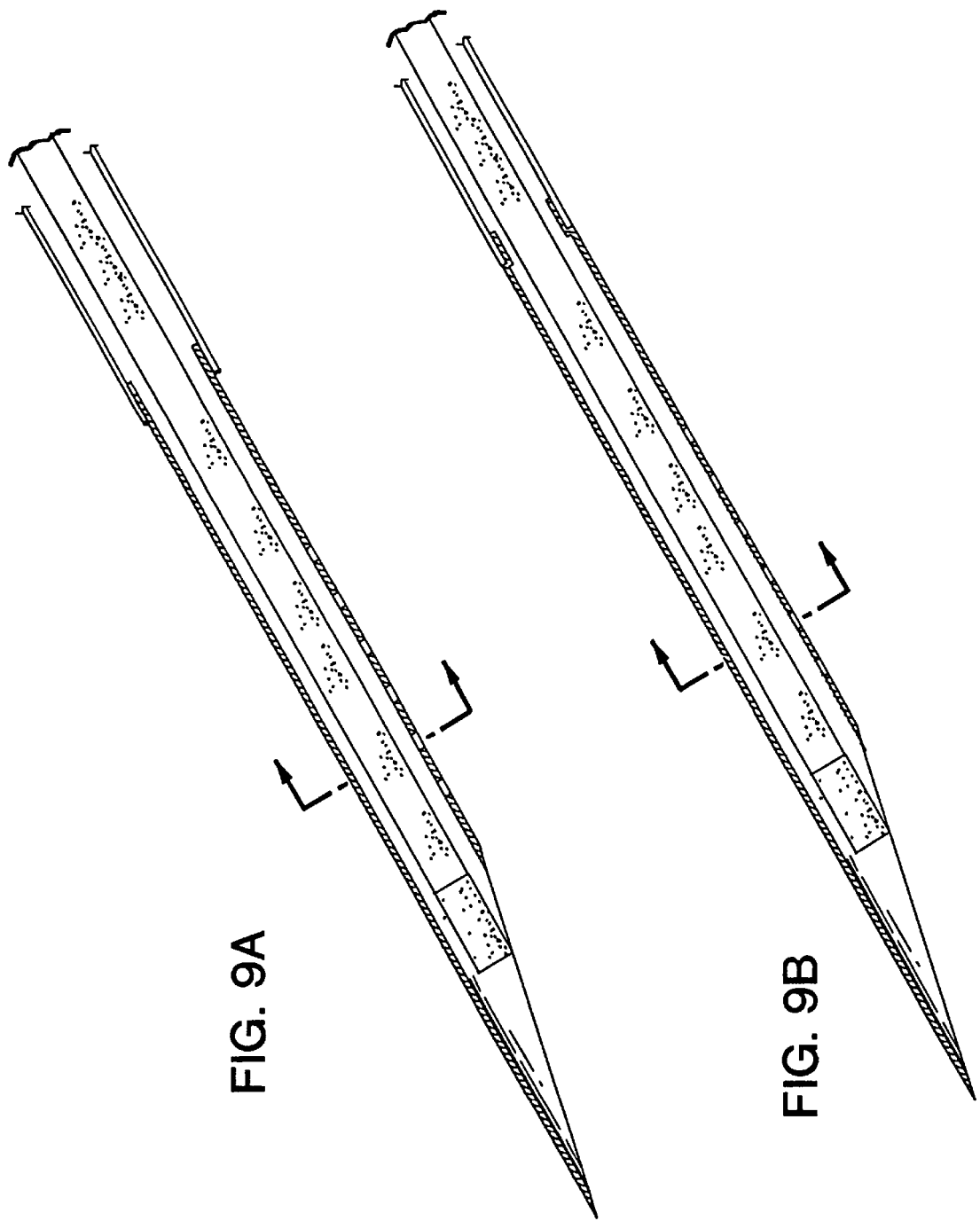
FIG. 9A diagrams a further alternative embodiment of a needle/optical fiber tip assembly of the invention, for practicing the methods of the invention showing the needle inserted within a movable inner catheter, having the optical fiber within the lumen of the needle and inner catheter/cannula, maintaining fluid communication through the needle. The arrows indicate the approximate location of the cross-sectional views depicted in FIGS. 2, 3, 7 and 11–13.
FIG. 9B diagrams an alternative embodiment of a device of the invention in which the needle is shaped at the proximal end with a flange to fit within an inner catheter so as to minimize perturbation of the outer surface of the catheter/needle, keeping the optical fiber within the lumen which allows fluid communication. The arrows indicate the approximate location of the cross-sectional views depicted in FIGS. 2, 3, 7 and 11–13.

As illustrated in FIG. 9A, a thin-walled inner catheter is disposed about the fiber and affixed to the needle so that fluid communication through the needle is obtained, without the catheter being thick or stiff, so the motive force can be applied solely to the optical fiber.

As illustrated in FIG. 9B, a symmetrical outer surface of the inner catheter to needle junction can be achieved by creating a flange at the proximal end of the needle, over which the inner catheter can be attached by adhesive. Apparatus similar to this design are relatively simple to manufacture at reasonable cost, and are relatively durable in use. Sample embodiments of such a device, have been used to each make more than 400 channels in bovine heart tissue with laser energy during in vitro testing.

Figure 10:
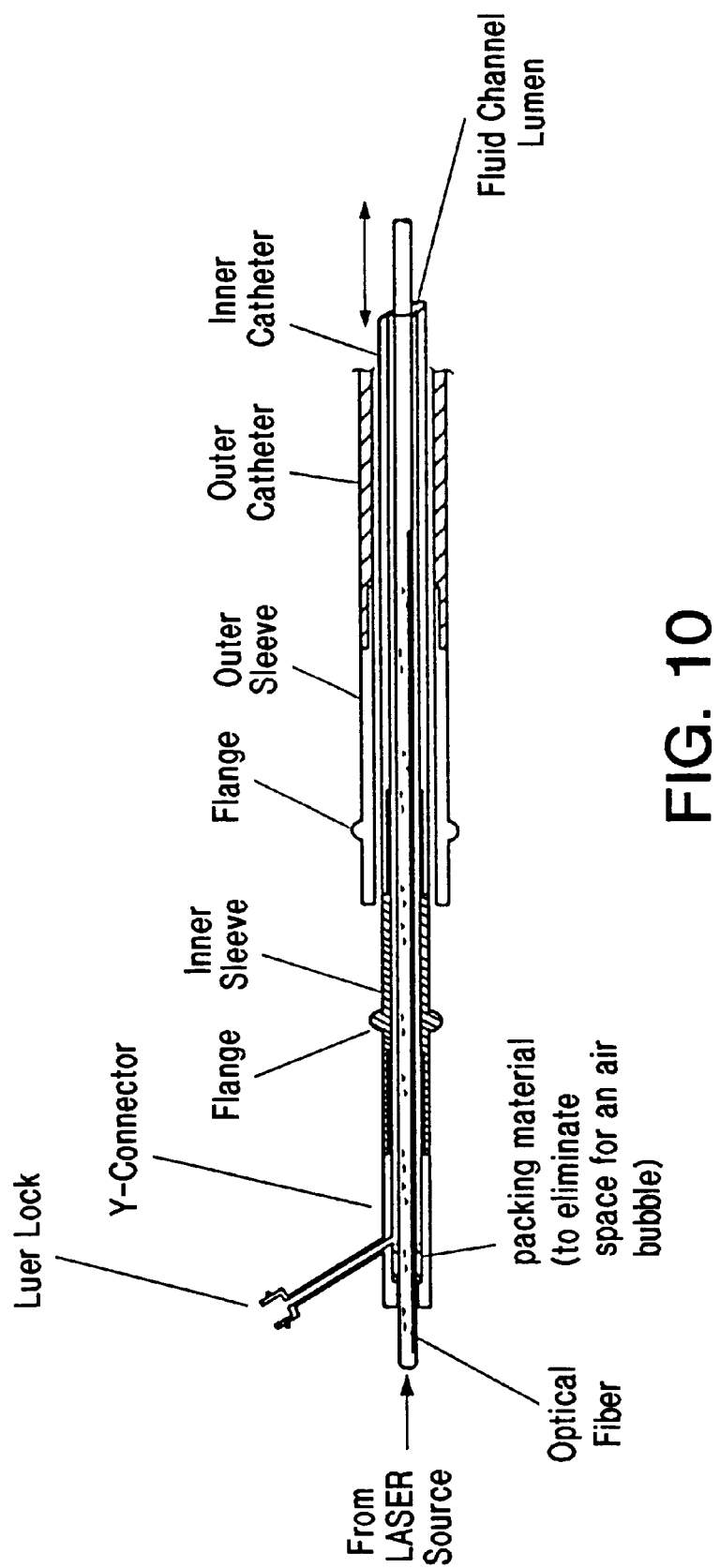
FIG. 10 illustrates the proximal end of the inner catheter of the device, which is held in place by fluid-tight attachment to the optical fiber. The optical fiber is not large enough to completely fill the lumen, and thus the inner cannula retains at least one fluid communication channel. A means for making fluid communication between the lumen of the inner cannula and an external fluid/drug/therapeutic source is shown having, in this embodiment a Luer lock at the end of a rigid, or flexible post, in fluid-tight attachment to the inner cannula.

As illustrated in FIG. 10, a luer lock attached to a port of a "y" connector attached by adhesive to the optical fiber at a point proximal to the distal end can be used for infusion of the liquid into the space between the fiber and an inner catheter attached by an adhesive to the distal end of a metal sleeve with a flange attached to the distal end of the "y" connector. The distal end of the metal sleeve is movably disposed within an outer sleeve (metal or other suitable material) attached by adhesive to the proximal end of an outer catheter.

Figure 14:
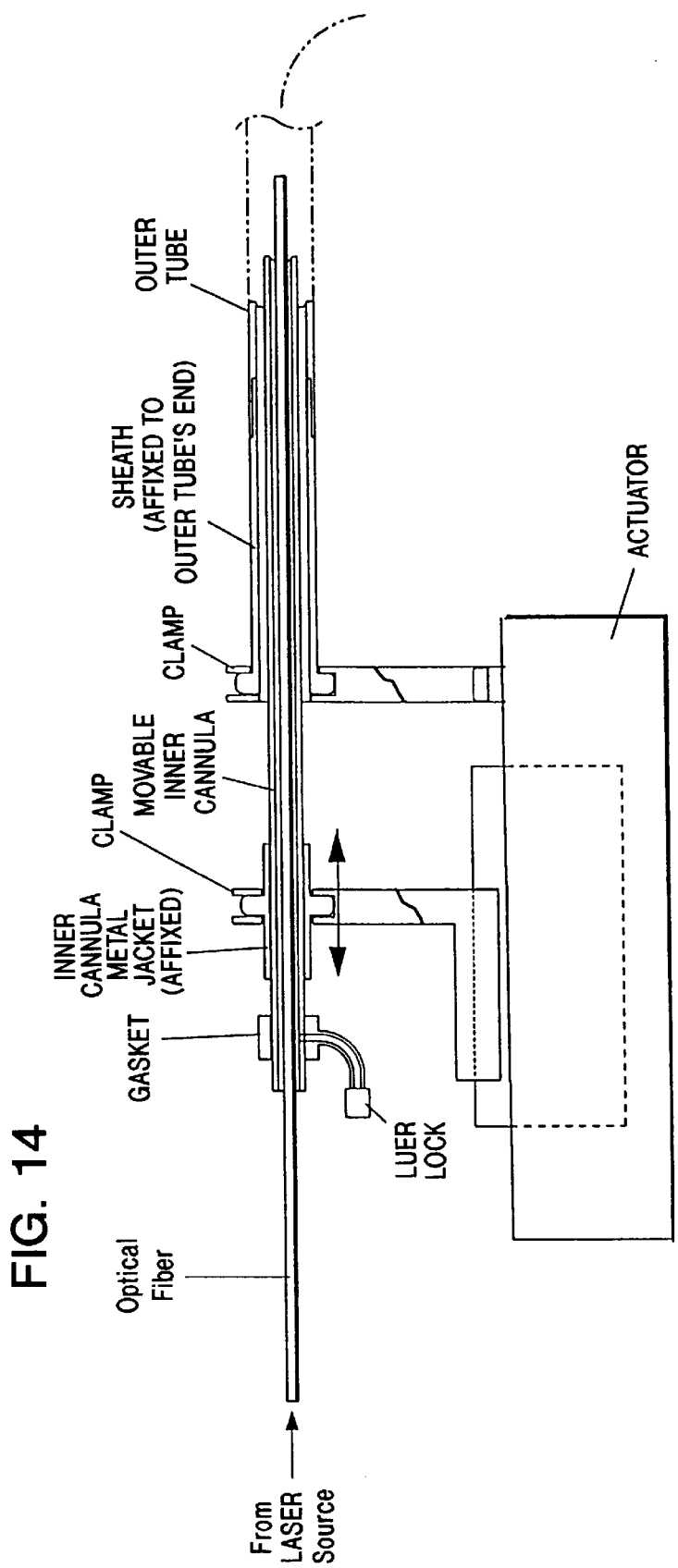
FIG. 14 is a cutaway cross sectional view of an additional embodiment of a device suitable for the practice of the present invention showing that the proximal end of the inner cannula is in fluid connection with a source of therapeutic agent by means of a gasket, and the optical fiber within the inner catheter is in communication with a Laser source.

As shown in FIG. 14, the flange of the inner metal sleeve is removably attached to the motive arm of the fiber advancement mechanism, and the flange of the outer metal sleeve is removably attached to the frame or body of said mechanism.

Devices for practicing the methods of the invention, the apparatus will have a source of pulsed laser energy optically connected to the proximal end of (opposite from the needle end) an optical fiber for delivery of laser energy to the needle/tip assembly. In a preferred embodiment the optical fiber extends into the needle from within the lumen of an inner catheter which is in fluid communication with a therapeutic or liquid drug source. As shown in FIGS. 11–13, three additional embodiments of the needle/optical fiber assembly of a device for practicing the invention are depicted. While described in terms of a needle, it is also contemplated, as discussed above, that a pointed, tapered, or blunt ended tip may also be suitably formed for making the mechanical puncture of the heart muscle, and thus may incorporate the features described herein with reference to a needle. Such a tip may be formed from suitable metal or plastic.

As shown in FIG. 11, fluid channels through the needle are cut within a buffer or jacket which fits around the optical fiber and within the bore of the needle/tip allowing fluid communication therethrough to the lumen of the inner catheter.

FIG. 12 depicts an embodiment similar to that of FIG. 11, however, protrusions from the inner surface of the bore of the needle crimp down upon the fiber optic jacket holding the fiber optic firmly within and in place, fluid channels being available as the spaces between the protrusions. Thus, in one tip embodiment, a needle contains protrusions within the bore of the needle which run substantially parallel with the length of the needle, or spirally along the length of the needle, and define channels which maintain fluid communication through the length of the needle when an optical fiber is fixed within the bore of said needle.

As shown in FIG. 13, instead of fluid exiting from the distal end of the needle, which can be affixed to the optical fiber's distal end with adhesive, one or more side ports proximal to the fixed distal end are provided to allow fluid to exit.

For attaching the fiber/inner catheter to the advancement mechanism, a metal sleeve with a flange can be disposed over and attached by an adhesive to the "y" connector affixed to the optical fiber ¼ to ½ of the length of the fiber from the laser source. The distal end of the metal sleeve is movably disposed within a second outer sleeve attached to the proximal end of an outer catheter. The second sleeve is attached to the advancement mechanism. The distal end of the outer catheter terminates within a handpiece with an actuator button.

Figure 15:
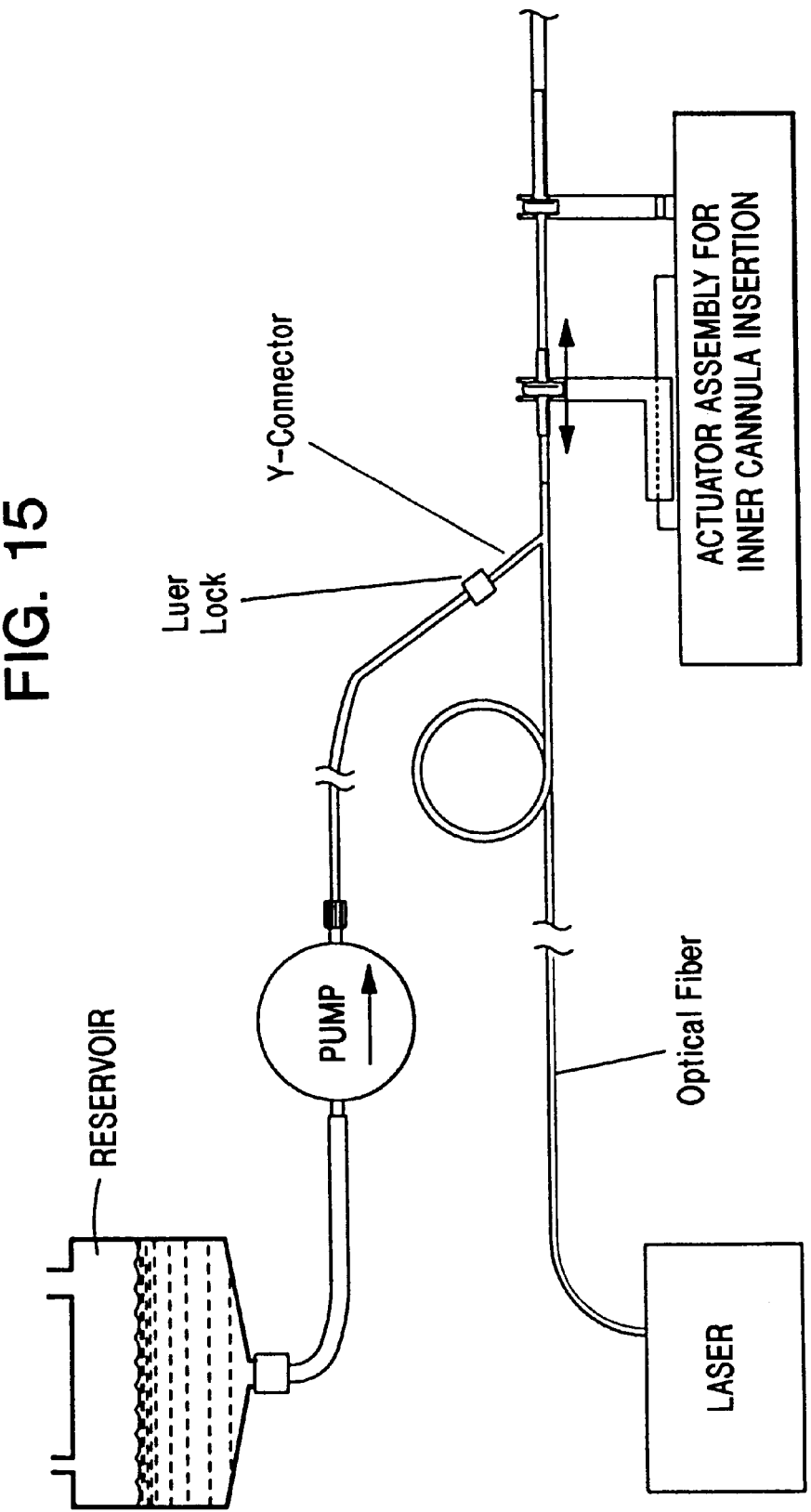
FIG. 15 is a schematic diagram showing an alternative embodiment of another device suitable for the practice of the methods of the invention, in which the drug is delivered by a pump into the inner catheter. This pump embodiment can also be adapted for injection into the surface of the heart during open surgery or in a endoscopic procedure through a puncture between the ribs, as well as percutaneous endoscopic procedures.

In FIG. 15, an alternative embodiment of the device of the invention is shown. In this embodiment, a pump and reservoir is in fluid communication through the inner catheter with the needle/optical fiber assembly.

Injection Devices

Figure 16:
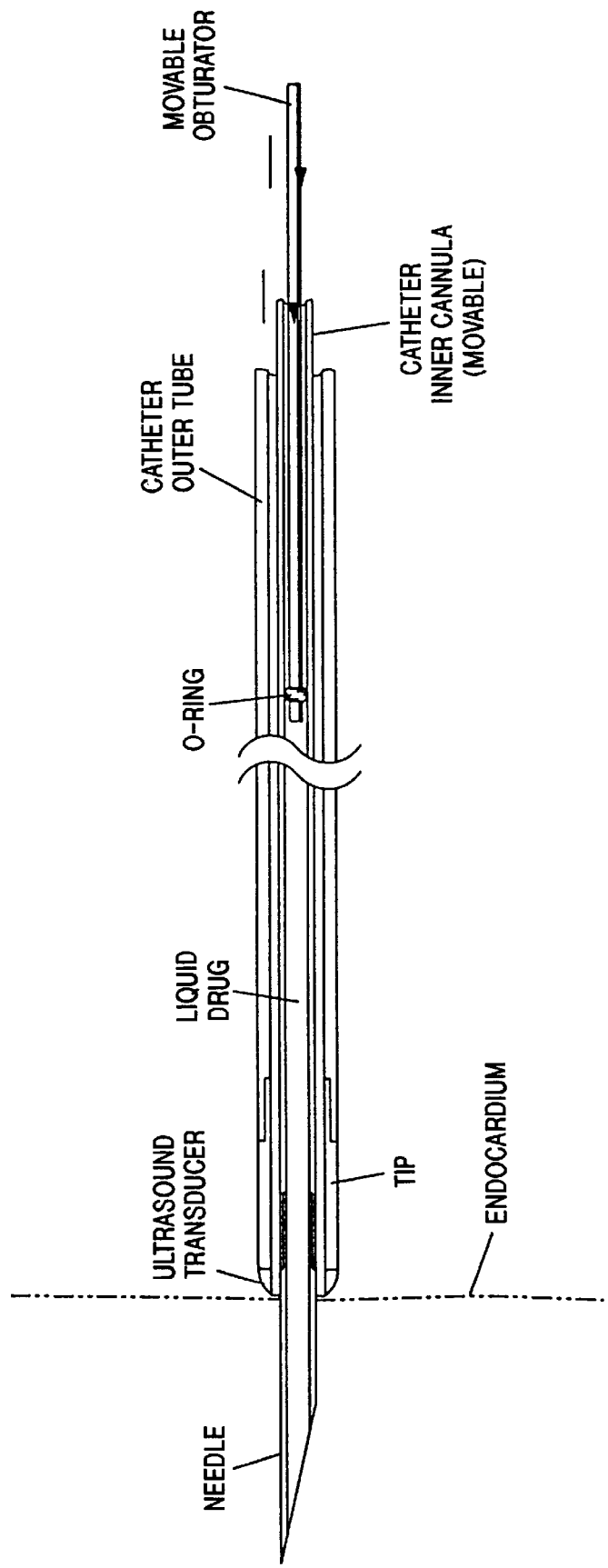
FIG. 16 is a cross section view of the distal end portion of an alternative embodiment of a device of the invention in which ultrasound transducers are used to estimate the thickness of the myocardial wall, and a movable obturator is inserted within the tube to assist injecting drug.

A further apparatus of the invention is shown in FIG. 16. In this embodiment, the distal end of the device is advanced into the heart wall or other tissue a selected distance, no laser energy is used to make a pocket, and a desired amount of a therapeutic agent is injected. In order to shorten the fluid path and reduce the amount and cost of fluid used in a procedure, instead of filling the entire inner catheter and then injecting an aliquot of fluid into the inner catheter to force an equal amount of fluid out of the needle, the entire amount of fluid of a therapeutic agent to be injected throughout the procedure is infused into the catheter. An optical fiber or flexible plastic rod, with an O-ring near the distal end is inserted into the inner catheter and advanced until fluid appears at the distal end of the needle. Then the fiber or plastic rod is advanced an appropriate distance, a desired amount of fluid exits the needle.

As shown in FIG. 17, aliquots of fluid are separated by bubbles of nitrogen (or other biocompatible gas). Aliquots of fluid are expelled from the needle by advancing an optical fiber or flexible plastic rod with an O-ring near its distal end, or by simply infusing saline to full the inner catheter and then in infusing aliquots of saline to displace the desired aliquot of drug containing fluid.

In FIG. 18, pellets of lyophilized agents or gelatin capsules containing the same are ejected from the needle by advancing an optical fiber or flexible plastic rod a distance equal to the length of a pellet or capsule, which can have a pointed or bullet shaped distal end.

It will be readily apparent from the foregoing detailed description of the invention and from the illustrations thereof that numerous variations and modifications may be effected without departing from the true spirit and scope of the novel concepts or principles of this invention.

While this invention is susceptible of embodiments in many different forms, this specification and the accompanying drawings disclose only some specific forms as examples of the invention. The invention is not intended to be limited to the embodiments so described, however. The scope of the invention is pointed out in the appended claims.

I claim:

1. A device suitable for administering a predetermined amount of a therapeutic agent into a mammalian heart myocardium comprising:

a catheter defining a fluid flow channel and having a distal end;

a hollow open ended puncturing tip in the form of a hollow needle at the distal end of the catheter and defining at least one fluid channel exiting the tip;

an optical fiber within the catheter and having a distal end extending into the fluid channel of the tip, the optical fiber together with the catheter defining a confined flow passageway in communication with the fluid channel in the puncturing tip, such that a therapeutic agent introduced via the confined flow passageway exists through the fluid channel of the tip, and wherein the needle contains protrusions within the bore of the needle which run substantially parallel with the length of the needle, or spirally along the length of the needle, and define channels which maintain fluid communication through the length of the needle when an optical fiber is fixed within the bore of the needle.

2. A device of claim 1 wherein said needle is beveled.

3. A device of claim 1 wherein said needle is crimped to grasp said optical fiber.

4. A device of claim 1 wherein said optical fiber is in a bundle of optical fibers.

5. A device of claim 1 wherein said fiber is covered by a buffer coat which defines channels within this coat that run substantially parallel with the length of the fiber, or spirally along the length of the fiber, and said channels maintain fluid communication through the length of the catheter.

6. A device of claim 1 wherein said tip contains more than one fluid channel exiting said tip.

7. A device of claim 1 wherein said tip contains an optical lens.

8. A device of claim 1, said tip and said catheter further having an external surface, and wherein said tip is attached to said catheter by means of a flanged fitting so as to leave a substantially smooth continuous surface between the external surface of the catheter and the external surface of the tip.

9. A device of claim 1 further comprising an outer catheter containing a lumen, wherein said catheter is inserted within said outer catheter and said device is suitable for insertion via a trocar into a patient.

10. A surgical device for forming a pocket within tissue and allowing injection of a therapeutic agent into said pocket through said device comprising:

a flexible outer catheter having a distal end;

a flexible movable inner catheter defining a fluid flow channel and distal end, movably located within said outer catheter lumen;

a flexible optical fiber for transmission of light energy, having a distal end, located within said inner catheter so as to permit fluid flow along the length of said inner catheter;

a rigid hollow tip having at least one fluid channel exiting said tip, attached to the distal end of said inner catheter and fixed to a portion of said optical fiber located within said hollow tip wherein said inner catheter flow channel remains in fluid communication with said tip channel, wherein said tip is a hollow needle; and an actuator operably connected to said inner catheter for selectively extending said inner catheter from said outer catheter such that said tip may mechanically penetrate tissue in opposition to the distal end of said outer catheter; and when said tip is further extended in conjunction with the transmission of light energy from said optical fiber, a cavity is formed within said tissue; and upon withdrawal of said tip a therapeutic agent may be injected via the inner catheter and tip into the cavity created by said light energy, wherein said needle contains protrusions within the bore of the needle which run substantially parallel with the length of the needle, or spirally along the length of the needle, and define channels which maintain fluid communication through the length of the needle when an optical fiber is fixed within the bore of said needle.

11. A device of claim 10 wherein said needle is beveled.

12. A device of claim 10 wherein said needle is crimped to grasp said optical fiber.

13. A device of claim 10 wherein said optical fiber is in a bundle of optical fibers.

14. A device of claim 10 wherein said tip contains more than one fluid channel exiting said tip.

15. A device of claim 10 wherein said tip contains an optical lens.

16. A device of claim 10, said tip and said catheter further having an external surface, and wherein said tip is attached to said catheter by means of a flanged fitting so as to leave a substantially smooth continuous surface between the external surface of the catheter and the external surface of the tip.

17. A device of claim 10 suitable for insertion via a trocar into a patient.

18. A device suitable for administering a predetermined amount of a therapeutic agent into a mammalian heart myocardium comprising:

a catheter defining a fluid flow channel and having a distal end;

a hollow open ended puncturing tip at the distal end of the catheter and defining at least one fluid channel exiting the tip; and a flexible drive cable within the catheter and having a distal end extending into the fluid channel and terminating in a rotatable burr, said cable together with said catheter defining a confined flow passageway in communication with the fluid channel in the puncturing tip wherein said tip is a needle and wherein said needle contains protrusions within the bore of the needle which run substantially parallel with the length of the needle, or spirally along the length of the needle, and define channels which maintain fluid communication through the length of the needle when an optical fiber is fixed within the bore of said needle, such that a therapeutic agent introduced via the confined flow passageway exists through the fluid channel of said tip.

19. A device suitable for administering a predetermined amount of a therapeutic agent into a mammalian heart myocardium comprising:

a catheter defining a confined flow passageway terminating in a hollow open ended puncturing tip which is a length of needle defining a bore with an inner-surface and wherein the bore forms part of the confined flow passageway;

an optical fiber in the catheter, extending into the bore and running the length of the needle;

a jacket layer surrounding the optical fiber, wherein the jacket layer is confined to the bore of the needle;

a plurality of protrusions extending lengthwise along the inner-surface of the bore and abutting the jacket layer to define at least one needle channel; and an electrical lead within the catheter and having a distal end terminating in an electrode which allows transfer of electrical energy to a tissue in contact with said electrode.

20. The device according to claim 19, wherein the needle further comprises a distal end comprising one or more side ports for allowing a therapeutic agent to exit the needle.

21. The device according to claim 19, wherein the catheter further comprises an inner catheter comprising a lumen with a first end attached to the needle and a second end attached to a therapeutic agent source to define a continuous enclosed passageway for the transfer of therapeutic agent from the therapeutic agent source and through the device and into a mammalian heart myocardium.

22. The device according to claim 21, wherein a pump is operably connected between the therapeutic agent source and the second end of the inner catheter to provide a pump action to drive the therapeutic agent from the source into the inner catheter and onward to the needle.

* * * * *